(12) United States Patent
Astorga-Wells et al.

(10) Patent No.: US 7,731,827 B2
(45) Date of Patent: Jun. 8, 2010

(54) METHOD FOR CAPTURING CHARGED MOLECULES TRAVELING IN A FLOW STREAM

(75) Inventors: Juan Astorga-Wells, Spanga (SE); Sang-Ryoul Park, Taejon (KR); Harold Swerdlow, Saffron Walden (GB); Gerald Jesson, Enkoping (SE); Ulf Lindberg, Knivsta (SE); Tomas Bergman, Jarfalla (SE); Hans Jornvall, Stockholm (SE); Mats Jonsson, Uppsala (SE)

(73) Assignees: PerkinElmer Health Sciences, Inc., Waltham, MA (US); Biomotif AB, Danderyd (SE); Hans Jornvall, Stockholm (SE)

( * ) Notice: Subject to any disclaimer, the term of this patent is extended or adjusted under 35 U.S.C. 154(b) by 1391 days.

(21) Appl. No.: 11/155,150

(22) Filed: Jun. 17, 2005

(65) Prior Publication Data

US 2005/0284762 A1 Dec. 29, 2005

(51) Int. Cl.
*B01D 61/44* (2006.01)

(52) U.S. Cl. ...................... 204/451; 204/542; 204/543; 204/544

(58) Field of Classification Search .................. 204/451, 204/542, 543, 544
See application file for complete search history.

(56) References Cited

U.S. PATENT DOCUMENTS 4,362,612 A * 12/1982 Bier ........................... 204/627

FOREIGN PATENT DOCUMENTS

| EP | 0 962 773 A1 | 12/1999 |
| GB | 2 211 859 A | 7/1989 |
| WO | WO 00 / 49396 | 8/2000 |
| WO | WO 02 / 43827 A2 | 6/2002 |

* cited by examiner

*Primary Examiner*—Arun S Phasge
(74) *Attorney, Agent, or Firm*—Fish & Richardson P.C.

(57) ABSTRACT

The invention relates to a method for capturing charged molecules of interest traveling in an electrolyte flow stream through an electrically non-conductive channel, comprising at least one anode and at least one cathode individually separated from said channel, but in electrical contact with said flow stream, by a conductive ion selective semi-permeable membrane. Said membrane interferes with the normal migration of ions towards its respective electrode, generating at least two zones of different electric field. Balance between hydrodynamic and electrical forces captures certain ions into the flow stream. it also relates to a device for performing the method.

38 Claims, 22 Drawing Sheets

A

B

A

B

METHOD FOR CAPTURING CHARGED MOLECULES TRAVELING IN A FLOW STREAM

BACKGROUND OF THE INVENTION

Biotech industries and laboratories are pushed to increase their productivity, efficiency and to lower their costs. Since most of the work involves liquid handling using a broad range of instruments and methods (e.g. pipettes, centrifuges, ovens, vortexes, chromatographic procedures and electrophoretic devices), the full integration of all these steps into a single analytical platform has become a tentative route to low-cost and high-throughput analysis.

The concept of integration by miniaturization of analytical systems stems from the micro-scale electronic industry, which managed to integrate multiple electronic devices into centimeter scale structures to perform a multitude of electrical processes. Such devices are faster, cheaper and easily assembled for industrial scale production. From this field, terms such as microchannels, microfluidics and micropumps emerge as solutions for the integration of different analytical assays and methods into a single format. In addition to high throughput and low costs, miniaturization leads to a reduction of sample, sample loses, and reagent consumption as well as of waste production.

An ideal fully integrated microfluidic device should permit complete analysis, from sample introduction (sample storage and injection), via pre-treatment (sample clean-up, buffer exchange, concentration, mixing, dilution, and derivatization), to the final analysis (e.g. DNA and protein sequence analysis, mass spectrometry), Although a significant progress has been achieved in this field, (e.g. use of electroosmotic flow for sample manipulation and injection, incorporation of Capillary electrophoresis (CE) for DNA, protein and peptide separations), systems are far from performing a broad range of functions. In the following, we examine some important problems that remain to be resolved.

Enzymatic reactions are widespread in clinical diagnosis, industrial applications and academic research. The miniaturization of reactions gives several advantages in relation to conventional schemes, such as faster reactions using less reactants, possibility to perform more assays per unit area and the potential to combine reactions with on-line separations. An important field where microreactors are advantageous in relation to present technologies is in drug discovery. Since the screening for new drugs normally involves a large number of inhibition or activation assays for a particular enzyme, miniaturization of the enzymatic reaction would increase the throughput and decrease the amount of reactants, decreasing the total cost of the assays.

The problems related to incorporation of enzymatic reactions into micrometer scale structures are mainly difficulties to mix two or more solutions (reagent and substrate) and the construction of incubation chambers. One-step reactions can be carried out if the reaction time is not more than a few minutes to keep the diffusion of the analytes along the microchannel at an acceptable level. If it is a multiple step reaction, the situation is more complicated since these often demand removal of the reagent or exchange of the buffer, which leads to mixing problems in nanoliter channels.

Another approach is immobilization of the enzyme to a solid support. As will later be explained, some technological problems arise with such an approach. In addition, another drawback of using solid supports is that the immobilization step cannot be carried out long before the use of the device, due to the possibility of contamination and enzyme degradation, Because of the practical disadvantages and shortcomings of the present technologies, those methods are unlikely to be implemented into fully integrated microfluidic devices.

Sample Pretreatment

The problem to incorporate sample pretreatment into the microchip format is related to the fact that most methods are based on solid stationary phases. The molecules of interest are captured via their affinity to the solid support and once the sample is retained, another solution is employed to wash away salts and other nondesirable compounds which is followed by release of the captured molecules into a buffer suitable for further analysis. Since the molecules are retained to the solid support during sample loading and washing, a significant preconcentration effect is generally obtained. However, there is a problem to incorporate this technology into the micrometer size channel format since the solid support must be mechanically packed using fits, or else be chemically bonded to the wall of the channel. Both approaches are difficult to apply in large-scale production. Another limitation is the specific physical interaction employed to retain the biomolecules of interest. Because of the broad distribution of size, polarity and other molecular properties (e.g. DNA, proteins, peptides), different solid supports are necessary to use in different analytical situations, This is clearly disadvantageous since a different chip would be necessary to manufacture for every new type of component processed. Lastly, fouling of the solid supports due to contaminants and small particulates in real samples limits their use and their capacity for re-use.

Capillary electrophoresis (CE) is a separation method with a high potential for use in the microchip format, which needs the incorporation of sample preparation to reach its full potential. The use of electrophoresis to separate DNA and proteins has been essential for the remarkable achievements of modern biological science. Although conventional slab gel electrophoresis is still very useful and widely used, CE is now the most powerful tool for DNA sequence analysis. In general, the advantages of CE are: higher speed, higher separation efficiency, reduced reagent volumes, and easier automation in relation to the slab gel technique.

The next step is implementation of CE into the chip format. Several parallel channels for electrophoresis can be built within a few centimeters including sample, buffers and waste reservoirs. Actually, Agilent Technologies is marketing a "Labchip" for DNA sizing, RNA analysis and protein separation. The microfabricated device is the simplest automated system for analysis of DNA, RNA and protein in the market. However, the system has no sample preparation capabilities. Desalting and removal of leftover nucleotides and templates is necessary for an adequate injection and separation of DNA. This step is, to some degree, the bottleneck in high-throughput DNA sequencing or analysis and eventually it will be a function necessary to implement onto chip systems. In addition, the use of small-bore capillaries limits the sample volume that can be injected to 1-10 nL and together with the short path-length available for optical detection systems, it is often necessary to include a preconcentration step for proper detection. Since proteins are not amplifyable, as is DNA, a preconcentration step is often needed for analysis by CE.

In summary, for a real analytical integration, the microfluidic approaches must find better methods to perform sample preparation and microreactions. The incorporation of these methods will lead to a significant increase in applicability to many fields, and thus increase the market share. For technological reasons, present technologies do not give a proper solution. The invention described here presents several advantages over the current technologies.

SUMMARY OF THE INVENTION

The present invention relates to a method for the capture of charged molecules in a micro-flow stream and to a membrane-based stacking device.

The device here described captures charged molecules in a spot in a flow stream without the help of solid supports or chemical binding. Different solutions can subsequently be injected into the device for sample clean-up or buffer exchange. Furthermore, the system can be used as a microreaction chamber by injecting reagents (charged or not charged) while the other reagent (charged) is being captured.

The capture of charged molecules is achieved by a combination of electrophoretic stacking and hydrodynamic sweeping effects, A detailed theoretical and experimental description of the invention is given in the following section.

BRIEF DESCRIPTION OF THE DRAWINGS

FIG. 1B illustrates an openchannel design, where the solution in the buffer reservoirs (9) can be freely circulated in the electrophoretic channel, but having the same electrical properties as in FIG. 1A.

FIG. 2A illustrates the movement of ions across the electrophoretic channel. FIG. 2B illustrates the position of the created zones with different electric field strength.

FIG. 12A shows a front sectional view of the device. FIG. 12bB shows a side sectional view across the electrolyte reservoirs (7), ion-selective membrane and the fluidic channel (1).

FIG. 21A shows a top view of the device. FIG. 21B shows a side sectional view across the electrolyte reservoirs (7). Ion-selective membrane (6) fluidic channel (1), and electrolyte reservoirs (7) can be observed.

DESCRIPTION OF THE INVENTION

Background

Figure 1:
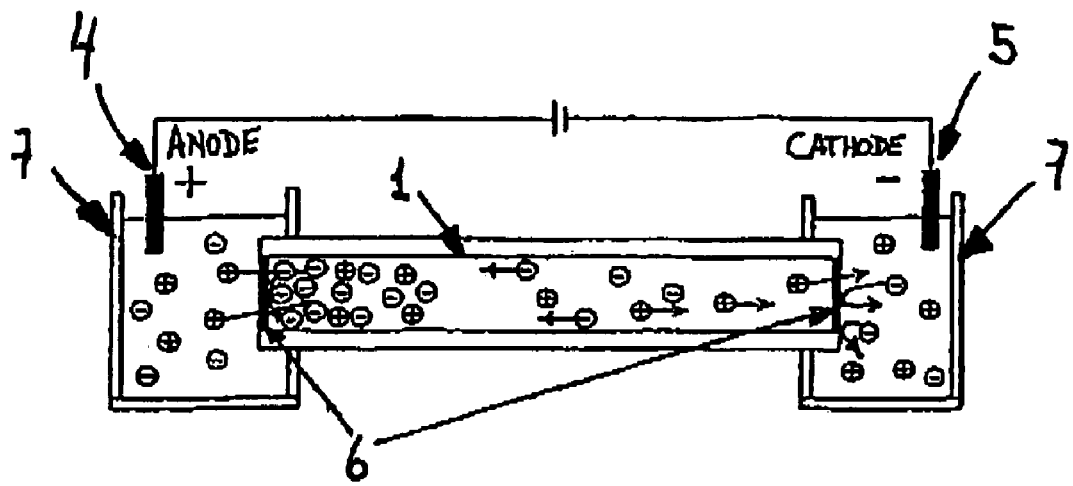
FIG. 1. Schematic diagram of a hypothetical device for creating areas of different ionic-concentrations in an electrophoretic channel. Ion-selective membranes (6) are placed between the electrodes (4, 5) and the electrophoretic channel (1). Said membranes do not permit the normal circulation of particular ions towards their respective electrodes creating zones with different ionic concentration, In FIG. 1A, the ends of an electrophoretic channel are sealed with cation selective membranes and positioned into electrolyte reservoirs (7) in a close-channel configuration.
Figure 1:
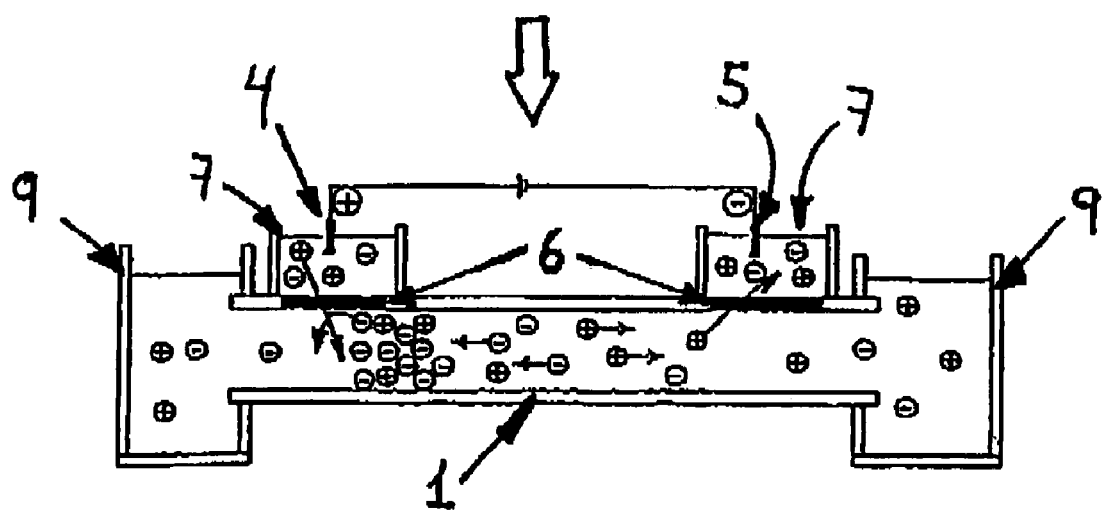

The invention relates to a method for capturing charged molecules of interest traveling in an electrolyte flow stream through an electrically nonconductive channel by creating zones with different local electric fields wherein certain ions are captured by stacking and hydrodynamic effects.

In electrophoresis, the term "stacking" refers to a group of preconcentration methods that manipulate the electrophoretic velocity of an analyte for band-sharpening. In normal electrophoresis, the electrolyte solution in the channel, electrode chambers and the sample itself have essentially the same characteristics, which forces all the ions of a particular analyte to move uniformly at the same speed. In contrast, stacking techniques use discontinuous buffers with different electrical and/or chemical properties with the purpose of focusing and concentrating the injected sample.

During electrophoresis, the electrophoretic velocity (cm's) of a certain ion is related to its particular electrophoretic mobility ($cm^2 V^{-1} s^{-1}$) and the electric field strength (Equation 1).

$$v_e = \mu \times E \qquad \text{Equation 1}$$

$v_e$=electrophoretic velocity
$\mu$=electrophoretic mobility
E=electric field

As E is defined as the potential difference (V in volts) per distance unit (centimeters) along the channel or other separation path and V is proportional to the current and resistance (Equation 2), a decrease in R will decrease E and therefore decrease the velocity of an ion moving in the electric field.

$$v_e = \mu \times E \qquad \text{Equation 2}$$

$v_e$=potential difference
$\mu$=current
R=resistance

As R is inversely proportional to the conductivity (Equation 3), a decrease in the conductivity in an electrical element with the same length and area, will cause an increase in the resistance and E, leading to an increase in the electrophoretic velocity of an ion situated in the electric field.

$$R = L/(\delta \times A) \qquad \text{Equation 3}$$

R=resistance
$\delta$=specific conductivity
L=length
A=area

As E is inversely proportional to the conductivity ($\delta$) (Equations 2 and 3), the electrophoretic velocity can be modified by moving a given ion through solutions of different conductivity.

As $\delta$ is usually directly proportional to the concentration of ions in the electrolyte solution, a decrease in the ionic strength will decrease $\delta$, increase R (Equation 3) and therefore increase E (Equation 2). For example, if a given ion is moving through a solution with a certain $\delta$ value and reaches an area with higher ionic strength, its electrophoretic velocity will be decreased due to the higher $\delta$ and therefore lower E value. Stacking methods employ this phenomenon to concentrate ions by using discontinuous electrolyte solutions with different conductivities or ionic strengths.

For example, stacking occurs when the sample is dissolved in a lower ionic strength solution than the electrophoresis buffer. In this case, the physico-chemical properties of the electrophoresis buffer are interrupted, resulting in local differences in the electric field strength in which ions move with different velocities toward the electrodes. As the local electric field strength is higher in the sample zone than in the rest of the electrophoretic channel, sample ions move rapidly towards the corresponding electrodes until they encounter the electrophoresis buffer boundary where they experience an electric field of lower strength causing their electrophoretic velocity to slow down. In this manner, the sample zone is focused or concentrated at the boundary between the sample zone and the electrophoresis buffer.

Since focusing requires discontinuous areas where ions move with different velocities, the injection of solutions with different electrical and/or chemical properties is indispensable.

The device and method described here is capable of creating a discontinuous zone in a continuous flowing buffer, allowing retention or capture of charged molecules by a different mechanism than that in preconcentration via stacking.

METHOD

General Description

Since in electrophoresis, anions and cations move to their respective electrodes (4,5), in theory it would be possible to accumulate one type (cations or anions) by using an ion-selective membrane (6) between the electrophoretic channel (1) and the electrodes (4,5). In this manner, if the device has a cation-selective membrane, anions (which cannot pass through the membrane) are going to accumulate close to the anodic membrane, while the cations will circulate freely between the channel and the electrode chamber. This is shown in FIG. 1A. In this manner, two zones with different ionic strengths are created. To permit sample injection into this channel, this design can be changed without modifying the system properties (FIG. 1B). Electrode buffer chambers (7) are arranged at the electrodes (4, 5).

Figure 2:
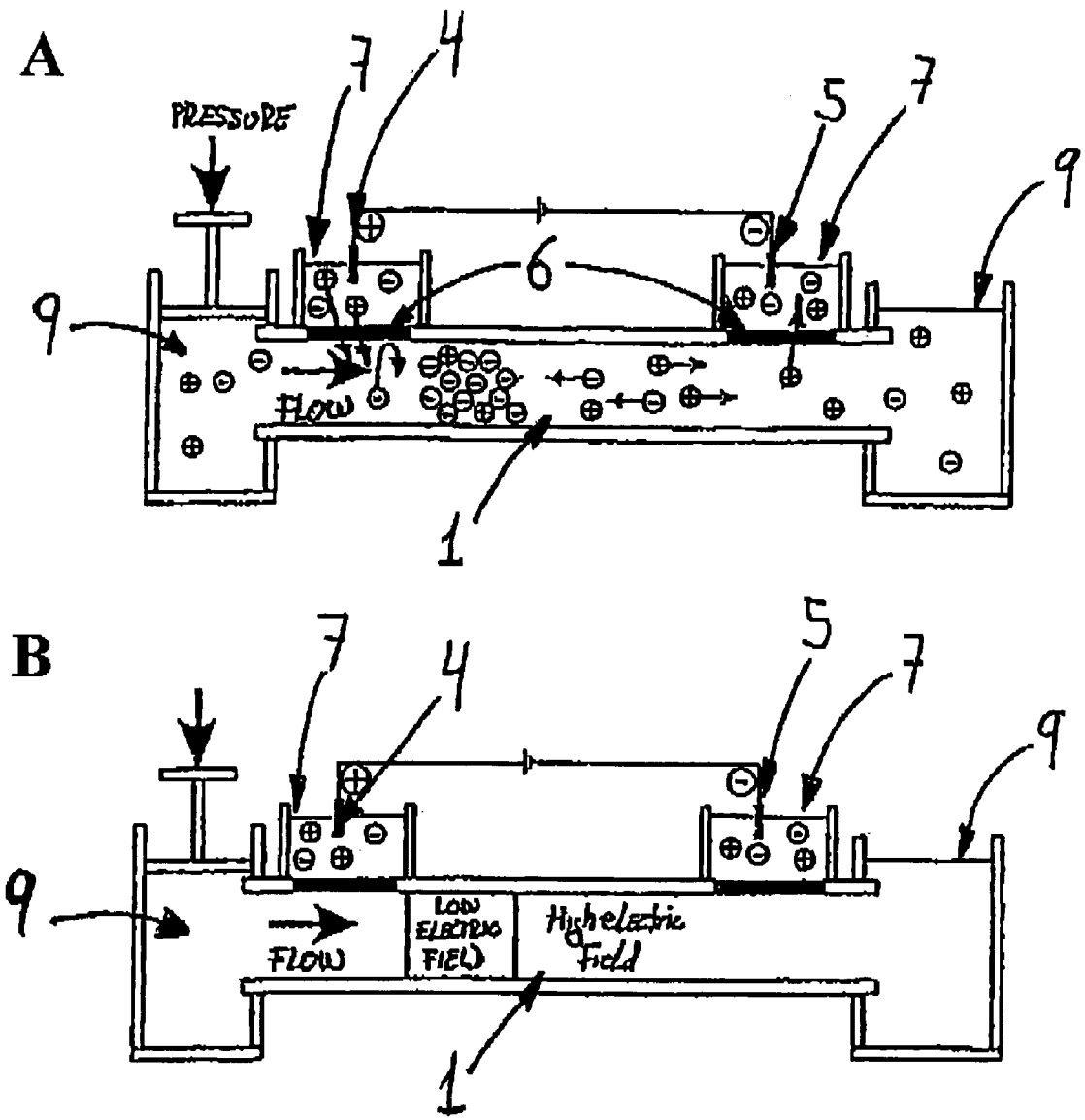
FIG. 2. Schematic diagram of a hypothetical device for creating a stacking zone into a flow stream. A hydrodynamic flow is applied to the electrophoretic channel (1), wherein the two zones of different ionic strength and electric field are created.

If the device is built with a cation-selective membrane (6), the stacking zone is created as follows. A hydrodynamic flow stream is applied in the electrophoresis channel (1) in such a manner that the high ionic strength zone is located upstream from the low ionic strength zone (FIG. 2A). The anode is located upstream and cathode downstream. Under this configuration, the hydrodynamic and electrical forces applied on an anion have opposite direction. Certain anions situated at the ion-concentrated zone, will be subject to a hydrodynamic force of higher magnitude than the electrical force, and will consequently be swept downstream towards the zone with higher electric field. When they enter into the zone of high electric field, the electrical force increases. For these ions, the magnitude of the electrical force becomes higher than the hydrodynamic force and they will therefore be pushed upstream against the flow.

When said ions again enter into the low electric field zone (ion-concentrated zone), the electrical force applied decreases, Since in this area the electrical force is weaker than the hydrodynamic force, said ions are again pushed downstream by the hydrodynamic force, where the process is repeated. By this mechanism, slow anions can be stacked or captured in a narrow band in the flow stream (FIG. 2B).

In the case mentioned above, the high electric field area is situated downstream from the low electric field strength area Empirical data supporting this mechanism (Table 1), examples and applications using the setup explained above are given in the Example 1, Example 2 and Example 3 in the Examples and Additional Data section. In a different set up, the polarity of the electrodes can be reversed, situating the cathode upstream, and the anode downstream, thereby changing the position of such zones. Now, the low electric field strength zone will be downstream from the high electric field strength zone. Under this mode, cations cannot pass through the anion-selective membrane, and are being pushed with an electrical force stronger than the hydrodynamic flow, are going to be retained on the surface of the membrane facing the channel. Examples of cations that cannot pass through cation selective membranes are peptides and proteins (in their cationic state), whose molecular size is too big to allow them to pass through the membrane pores.

The same theoretical model can be applied if the device has an anion selective membrane. In this case, slow cations will be captured between the ion-concentrated zone and the low ionic strength area, when the zones are situated upstream and downstream, respectively (cathode upstream and anode downstream). On the other hand, anionic macromolecules, whose molecular sizes are too big to allow their passage through the membrane, are going to be retained on the internal surface of the membrane. Examples of such molecules are DNA and proteins or peptides (in their anionic state), when the zones of high electric field and low electric field are situated upstream and downstream, respectively (cathode downstream and anode upstream).

Detailed Description of the Method

The invention relates to a method for capturing charged molecules of interest traveling in an electrolyte flow stream through an electrically non-conductive channel, comprising at least one anode and at least one cathode individually separated from said channel, but in electrical contact with said flow stream, by a conductive ion selective semi-permeable membrane. Said membrane permits the selective passage of either negatively (anion selective membrane) or positively (cation selective membrane) charged ions, which interferes with the normal circulation of ions towards its respective electrode, thereby accumulating inside the channel ions that are not allowed to pass through the ion selective membrane, and by this means generating at least two zones with different ionic strength, conductivity and local electric field strength; whereby modifying the selectivity of the ion-selective membrane (cation- or anion-selective) or/and the position of the anode and cathode (upstream or downstream);

i) the zone with lower electric field strength is situated upstream from the one with higher electric field strength; and a hydrodynamic force is applied to ions attracted by the electrode situated upstream, which is greater than and in opposition to the electrical force generated on the charged molecules of interest situated at the zone with lower local electric field strength; therefore pushing the charged molecules of interest downstream towards the zone with higher electric field strength, and lower than and in opposition to the electrical force generate on the zone with higher electric field strength, therefore pushing back again the charged molecules of interest upstream towards the zone with lower electric field strength; where the process is repeated, thereby stacking the ions between the zones with different electric field strength;

ii) the zone with higher electric field strength is situated upstream from the one with lower electric field strength; wherein charged molecules, attracted by the up stream electrode, pulled with an electrical force greater than the hydrodynamic force of the flowing stream, and not allowed to pass through the ion selective membrane are retained on the surface of the membrane.

In this manner, if said membrane is a cation selective membrane which is permeable to cations but not to anions, therefore interfering with the normal circulation of anions, but not cations, towards its respective electrodes, thereby accumulating inside the channel anions that are not allowed to pass through said membrane, will generate at least two zones with different ionic strength, conductivity and local electric field strength; where:

i) the anode is situated upstream from the cathode, thereby the zone with higher ionic strength and lower electric field strength is situated upstream from the one with lower ionic strength and higher electric field strength; and a hydrodynamic force is applied, which is greater than and in opposition to the electrical force generated on a negatively charged molecules of interest situated at the zone with lower local electric field strength; therefore pushing said molecules downstream towards the zone with higher electric field strength, and lower and in opposition than the electrical force generated on the negatively charged molecules of interest at the zone with higher electric field strength, therefore pushing back again said molecules upstream towards the zone with lower electric field strength; where the process is repeated, thereby stacking said molecules between the zones with different electric field strength;

ii) the cathode is situated upstream from the anode, thereby the zone with higher ionic strength and lower electric field strength is situated downstream from the lower ionic strength and higher electric field strength zone; where the positively charged molecules of interest, pulled with an electrical force greater than the hydrodynamic force of the flowing stream, and which are not allowed to pass through the ion selective membrane, are retained at the surface of the membrane.

In the other hand, if said membrane is an anion selective membrane which is permeable to anions but not to cations, therefore interfering with the normal circulation of cations, but not anions, towards its respective electrode, thereby accumulating inside the channel cations that are not allowed to pass through said membrane, will generate at least two zones with different ionic strength, conductivity and local electric field strength; where i) the cathode is situated upstream from the anode, thereby the zone with higher ionic strength, and lower electric field strength is situated upstream from the one with lower ionic strength, and higher electric field strength; and a hydrodynamic force is applied, which is greater than and in opposition to the electrical force generated on the positively charged molecules of interest situated at the zone with lower local electric field strength; therefore pushing the said molecules downstream towards the zone with higher electric field strength, and lower and in opposition than the electrical force generate on the positively charged molecules of interest at the zone with higher electric field strength, therefore pushing back again the said molecules upstream towards the zone with lower electric field strength; where the process is repeated, thereby stacking said molecules between the zones with different electric field strength;

ii) the anode is situated upstream from the cathode, thereby the zone with higher ionic strength and lower electric field strength is situated downstream from the lower ionic strength and higher electric field strength zone; where negatively charged molecules of interest, attracted by the upstream electrode, pulled with an electrical force greater than the hydrodynamic force of the flowing stream, and which are not allowed to pass through the ion selective membrane are retained at the surface of the membrane. After being captured, the captured molecules may be released by modifying the applied flow rate and/or electrical field and/or by changing the electrolytic medium to a medium with a different ionic strength, pH or conductivity.

The original solution in which the molecules are trapped could be exchanged to another solution that is injected into the system. The new solution can be selected to be more suitable for the next analytical step, or it can contain molecules that react with the trapped charged molecules to make them suitable for further analysis and detection.

Since the system captures charged molecules passing through an electric field in a flow stream, several microliter of sample can be injected continuously into the system and released as a concentrated band of a few nanoliter volume for further manipulation and analysis.

Also, since ions have different mobilities, it would be possible to selectively retain some ions in the system by modifying the flow rate and/or the voltage applied. For biomolecules with a high electrical mobility, the electrical force would exceed the drag force of the flow and they would be captured, for biomolecules with a low electrical mobility the drag force would exceed the electrical force and they would be swept out of the system. In this manner, the capture device would act as a separation device.

By using several electrodes and corresponding ion selective membranes in the channel, different electric fields may be applied between the electrodes, creating several zones with different local electric field strengths, so that different charged molecules of interest with different electrical mobilities are captured at different zones along the fluidic channel.

The electric field differences are subsequently removed between one pair of electrodes after the other, or between all of them at the same time, thereby releasing said molecules that were captured at different zones along the fluidic channel, sequentially or all at the same time, respectively.

Figure 19:
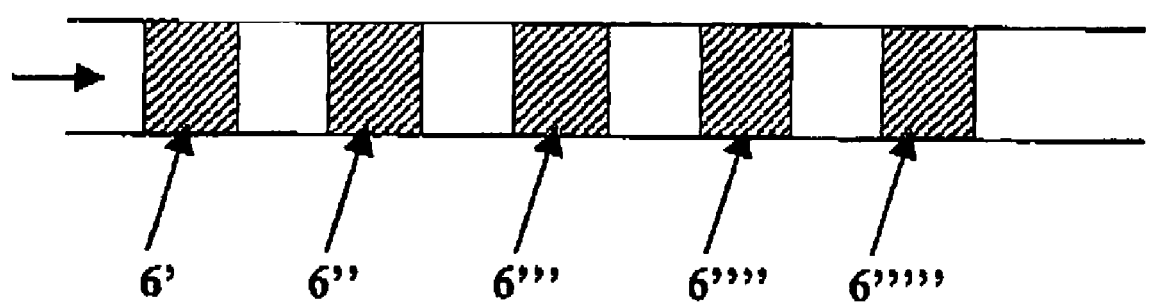
FIG. 19 illustrates a multiple ion-selective membrane configuration.

Thus, several ion selective membranes and their respective electrodes can be placed and connected in series along a channel as is depicted in FIG. 19. By applying a low potential between the first (6') and the second ion selective membrane (6"), as numbered from the upstream side, biomolecules with a relatively high electrophoretic mobility will be captured. Between the second (6") and the third (6''') ion selective membrane, a slightly higher voltage is applied and biomolecules with a relatively lower electrophoretic mobility are captured. By adding several ion selective membranes, biomolecules with different electrophoretic mobility will be captured at different locations along the channel. As the voltage difference is removed between pairs of ion selective membranes, the biomolecules that are trapped between them can be sequentially released. This can be made preferable by removing the electric field from the electrodes located most downstream and then sequentially removing the electric field from the other electrodes situated more upstream.

Figure 20:
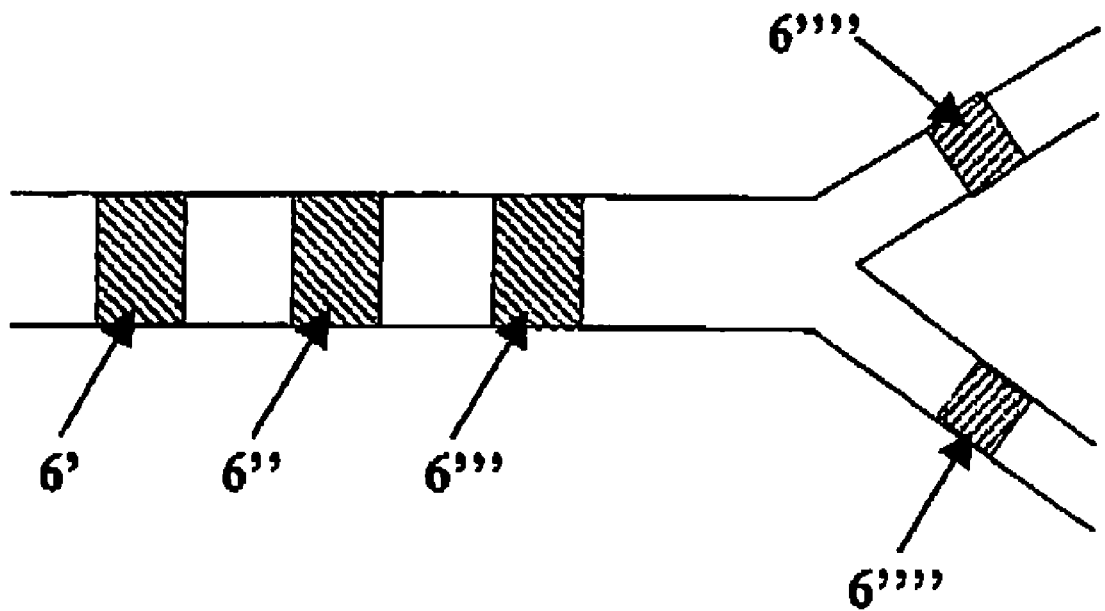
FIG. 20 illustrates a multiple ion-selective membrane configuration with one pair of sub-channels.

The channel may be divided into one ore more sub-channels each comprising one or more electrodes and corresponding ion selective membranes (FIG. 20). Molecules that are stacked and released in the channels are then guided along one or more sub-channels by modifying the electric field between the ion selective membranes. As trapped molecules are released, they can be guided along different branches in a crossing, just by manipulating the voltage difference between ion selective membranes.

The sub-channels may further comprise one or more inlets and outlets so that molecules stacked and released in the channels may be guided along one or more sub-channels by modifying the applied flow rate and/or electrical field and/or by changing the electrophoretic medium to a medium with a different ionic strength or conductivity.

While the charged molecules of interest are captured according to the invention, the electrolyte medium can be replaced by a second medium by means of injecting another fluid media into the fluidic channel. This can be used to desalt the charged molecules of interest by using a second medium containing less salt (see application number 3 in the "Particular non-limiting applications" section).

It is also possible to perform reactions and use a second medium containing molecules that are brought into contact with charged molecules of interest and interact and/or react.

The following pairs of molecules can be allowed to interact using a process according to the invention; antigen (antibody), antibody (antigen), hormone (hormone receptor), hormone receptor (hormone), polynucleotide (complementary polynucleotide), avidin/streptavidin (biotin), biotin (avidin/streptavidin), enzyme (enzyme substrate), enzyme substrate (enzyme), enzyme (enzyme inhibitor), enzyme inhibitor (enzyme), lectins (carbohydrate), carbohydrate (lectins), lipid (lipid binding protein), lipid binding protein (lipid), lipid (membrane-associated protein), membrane-associated protein (lipid), polynucleotide (polynucleotide binding protein), polynucleotide binding protein (polynucleotide), receptor (transmitter), transmitter (receptor), drug (target), target (drug), protein (protein), protein (polynucleotide), polynucleotide (protein), DNA (DNA), DNA (RNA) and RNA (DNA).

These molecules may react in a synthesis or a degradation reaction. The reaction may e.g. be a proteolytic digestion of a protein or any structural modification of a protein or a peptide or of DNA or RNA, Such as reaction may also be a DNA, RNA, protein and peptide synthesis.

Device

Detailed Description

The invention also relates to a device for capturing charged molecules of interest traveling in a hydrodynamic flow stream of an electrolyte medium comprising at least one channel (1) built into an electrically non-conductive material, and at least one inlet (2) and one outlet (3) into said channel (1) for injection and exit of said medium and a system providing a continuous flow of said medium into the said channel, and at least one anode (4) and at least one cathode electrode (5), wherein said electrodes (4, 5) are individually separated from said channel (1), but in electrical contact with said electrolyte medium by each a conductive membrane (6), characterized in that said membranes (6) are ion selective membranes, which permit the selective passage of certain charged ions or molecules and blockade of others.

The ion selective membranes may be cation selective or anion selective. The channel may have any form and be arranged in any direction. Thus, the channel may be substantial vertical such as a substantially vertical column. The channel may also be substantially horizontal. One or more channels may be present. Thus, one ore more channels may be arranged in a substantially planar device.

The device according to the invention comprises a microfluidic system, which accumulates ions into at least one zone in at least one sample plug. The device allows for the creation of high and low ionic strength areas, where with the help of a hydrodynamic opposite force, ions are trapped.

The semipermeable membranes used according to the invention may be any kind of membranes which permit the selective passage of certain charged ions or molecules and blockade of others. Good examples of this membrane are ion selective semi-permeable membranes. Said membranes are selective to one type of ions, positively (cation selective semipermeable membrane) or negatively charged (anion selective semi-permeable membrane).

While in the present invention is preferred to use ion selective semi-permeable membranes, due to their high selectivity and good electrical conductivity, any kind of membrane or material which is selective to one or more particular ions and blockade of others should be considered.

The ion permeable membranes that can be used in the present invention are essentially sheets of ion-exchange resins. They usually also contain other polymers to improve mechanical strength and flexibility. The resin component of a cation-exchange membrane would have negatively charged groups (e.g. $—SO_3$) chemically attached to polymer chains (e.g., styrene/divinylbenzene copolymers). Ions with a charge opposite to the fixed charge (counter ions) are freely exchanged at these sites. The concentration of counter ions (e.g. $Na^+$) is relatively high; therefore, counter ions carry most of the electric current through the membrane. The fixed charges attached to the polymer chains repel ions of the same charge (co-ions), in this case the anions. Since their concentration in the membrane is relatively low, anions carry only a small fraction of the electric current through a cation permeable membrane, Examples of such membranes are: Nafion (a trademark of E.I. DuPont de Nemours, Wilmington, Del., USA), Tokuyama Soda Neosepta (trade-mark) CMX, CM-1 and CM-2, Asahi Glass Selemion (trade-mark) CMV and CSV and Raipore R4010 and R-1010 (trade-marks of RAI Research Corporation, Hauppauge, N.Y., USA). On the other hand, attachment of positive fixed charges (e.g. $—NR_3^+$ or $C_5H_5N^+R$ where commonly $R=CH_3$) to the polymer chains forms anion permeable membranes, which are selective to transport of negative ions, because the fixed $—NR_3^+$ groups repel positive ions. Examples of such membranes are: RALEX AME and RALEX AM (trade-marks of MEGA a.s. Czech Republic), which have $R—(CH_3)_3N^+$ groups on different polymer substrates.

Alternatively, the semipermeable regions used according with the invention may be created by constructing porous sections along the non-conductive channel by: chemical etching (e.g. standard photolithographic procedures followed by wet and/or dry chemical etching), electroetching or by other physico-chemical method (e.g. ion-bombarding or abrasive-procedures or laser-ablation). The porous section should permit the selective passage of certain charged ions or molecules and blockade of others. The created porous region may also be treated to achieve these characteristics by incorporate charged chemical group into its structure (e.g. casting said region with ion selective semi-permeable polymers (covalently or non-covalently) or by covalent binding of negatively or positively charged groups).

As explained above several electrodes and corresponding ion selective semi-permeable membranes may be provided in the channel. Further, several channels can be arranged in the same electrical non-conductive material.

The fluidic channel may be present in an electrically non-conductive planar support, by building one or several parallel and/or non-parallel trenches and bonding on top a second electrically non-conductive planar support. In such a device the walls of the electrically non-conductive planar support that structures the fluidic channel may be interrupted by sections of ion selective membranes zones which are in electrical contact with at least one cathode and one anode, and by these means make electrical contact with the electrolyte flow stream.

The invention described can readily be incorporated into the two basic microfluidic platforms: capillary format and planar structures.

Capillary Format

Figure 3:
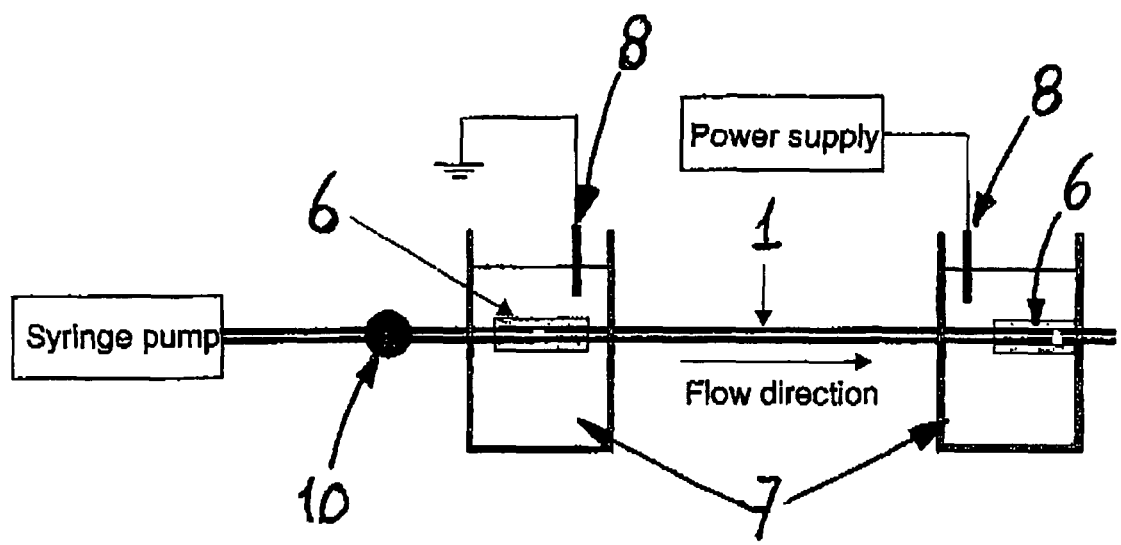
FIG. 3. Schematic representation of the microfluidic electrocapture device. The device has the same characteristics than FIG. 2. A valve (10) connects the microfluidic device with a syringe pump that produces a hydrodynamic flow. Electrodes (8) positioned into electrolyte reservoirs (7) serve as cathode or anode depending on polarity of the electric potential applied by power supply.

The device can be incorporated into capillaries (tubes of micrometer size-range diameter) of non-conductive materials (e.g. glass, fused silica, or any non-conductive polymer). The manufacture includes the incorporation of two or more zones where the non-conductive material is replaced by the ion-conductive material. Examples of this format are shown in FIG. 3 and used in Example 1, Example 2 and Example 3. The ion-selective areas can be made by incision or making a crack in different sections along the capillary, whereafter the openings are sealed with the ion-selective conductive material. The sealing can be achieved by using a membrane of the ion-selective material (tube grapping the capillary of gluing a planar membrane). The device can also be built by dropping a volatile solution containing the ion-selective material onto the cracks. After the solvent has evaporated, a film of ion-selective material will cover the crack. Any other means to incorporate the ion conductive material into two or more zones in the non-conductive material do well to achieve the same purpose. The capillary is then placed into reservoir chambers that can be filled with a liquid or a gel. Electrodes are placed in the reservoir and connected to a power supply.

Planar Structures

Figure 11:
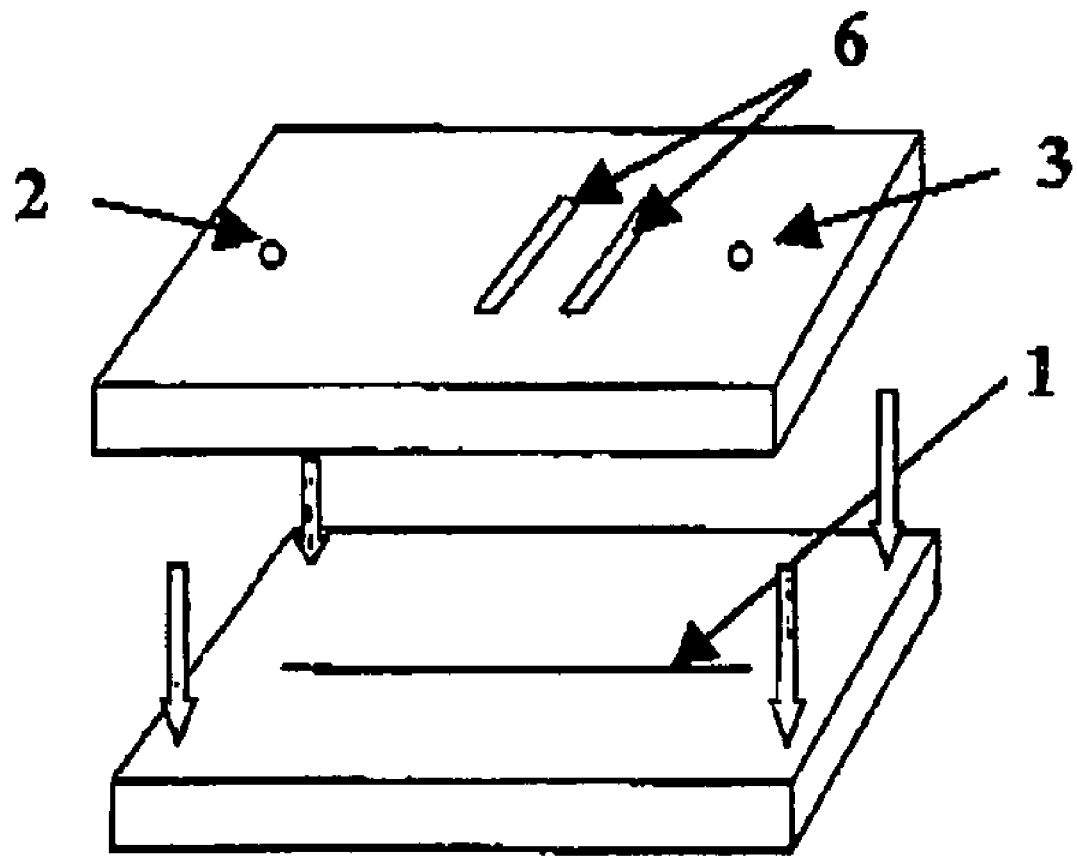
FIG. 11 illustrates a planar design of the device according to the present invention. A trench is made in a planar structure. To build the fluidic channel, the trench is covered with a second planar structure. Inlet (2) and outlet (3) holes are made in the upper planar structure. A region in the upper planar structure material is replace with ion selective material (6).
Figure 12:
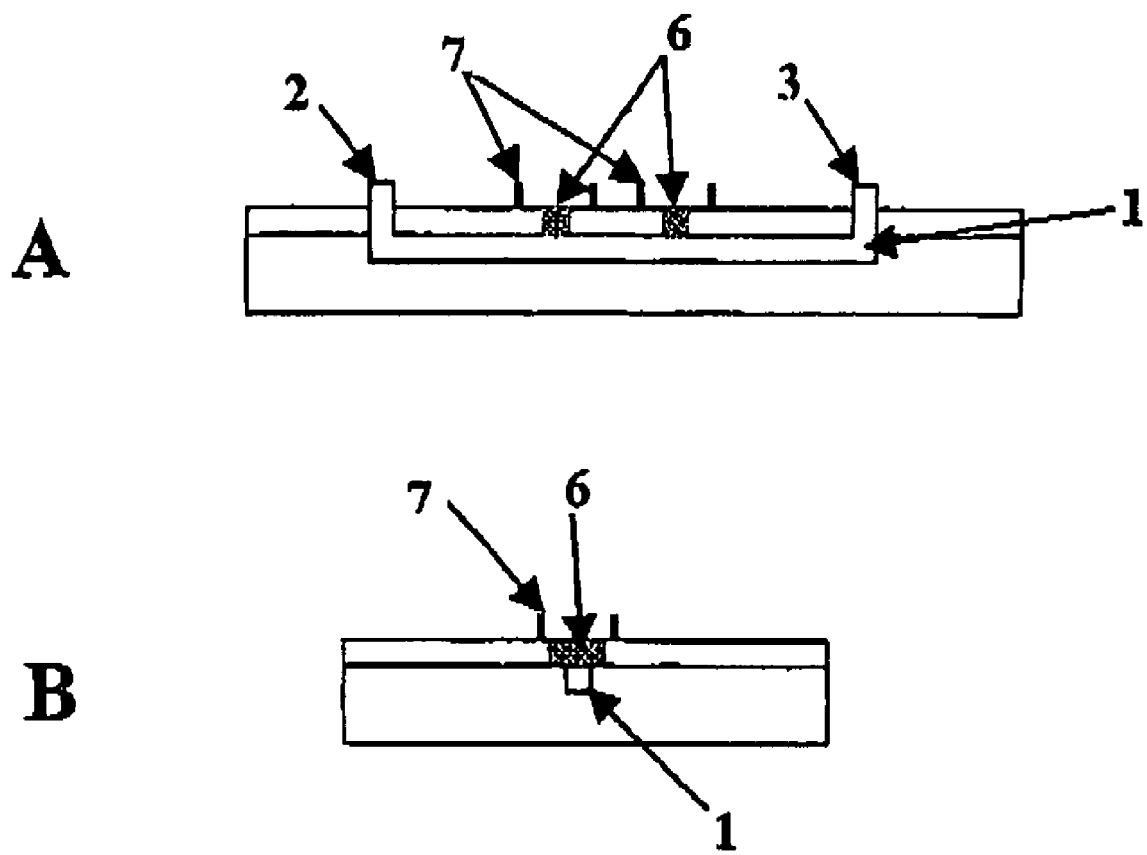
FIG. 12 illustrates a planar design shown in FIG. 11 after bonding.

This approach involves the manufacture of various microfluidic structures (e.g. channels and fluidic connections) and electrical contacts in a non-conductive planar support (e.g. glass, quartz, silicon, oxidized silicon, fused silica and polymeric substrates (e.g. acrylics)). A channel (1) is etched, molded, ablated or imprinted in a planar surface. Both structures can be made of the same material or a combination of non-conductive materials. The ion-selective areas (6) may be incorporated into the same structure or into another planar structure (FIG. 11). To create the fluidic channel, the planar surface that has the trench or channel (1) can be sealed by bonding to another planar surface. One (or both) planar structure(s) can contain appropriate structures to allow fluidic connections. The resulting device is depicted in FIG. 12. In the planar structures of FIG. 11 and FIG. 12, (1) is the trench or channel, (2) is an inlet hole, (3) is an outlet hole and (6) are semipermeable selective areas or membranes.

Figure 13:
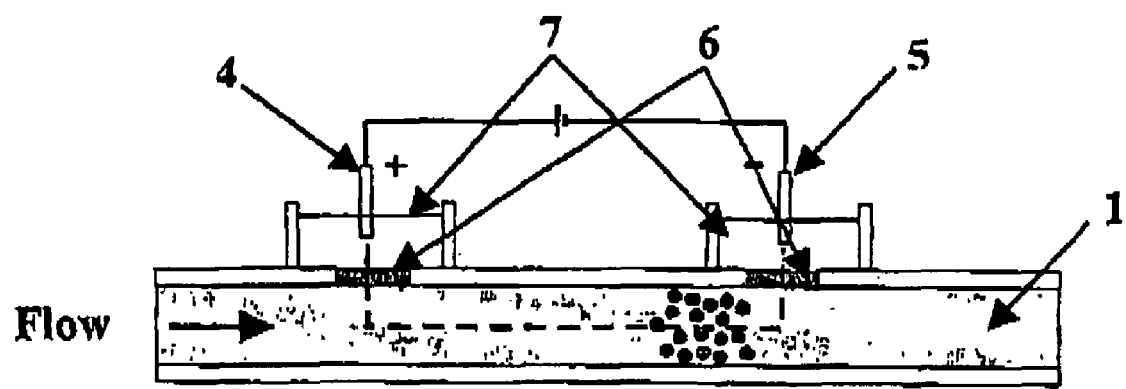
FIG. 13 illustrates the planar design with electrodes (4, 5) in operation. Under this setup (cathode upstream (4) and the a ion-selective membrane (6) being a cation-selective membrane), dark spheres represent captured anions.

FIG. 13 shows a schematic view of the capture device built into planar structures, where the ion selective materials (6) are assembled in one of the structures and in contact with the fluidic channel (1). Electrolyte reservoirs (7) are attached to the same structure allowing the correct electrical contact between the electrodes (4, 5) and the fluidic channel (1).

Figure 14:
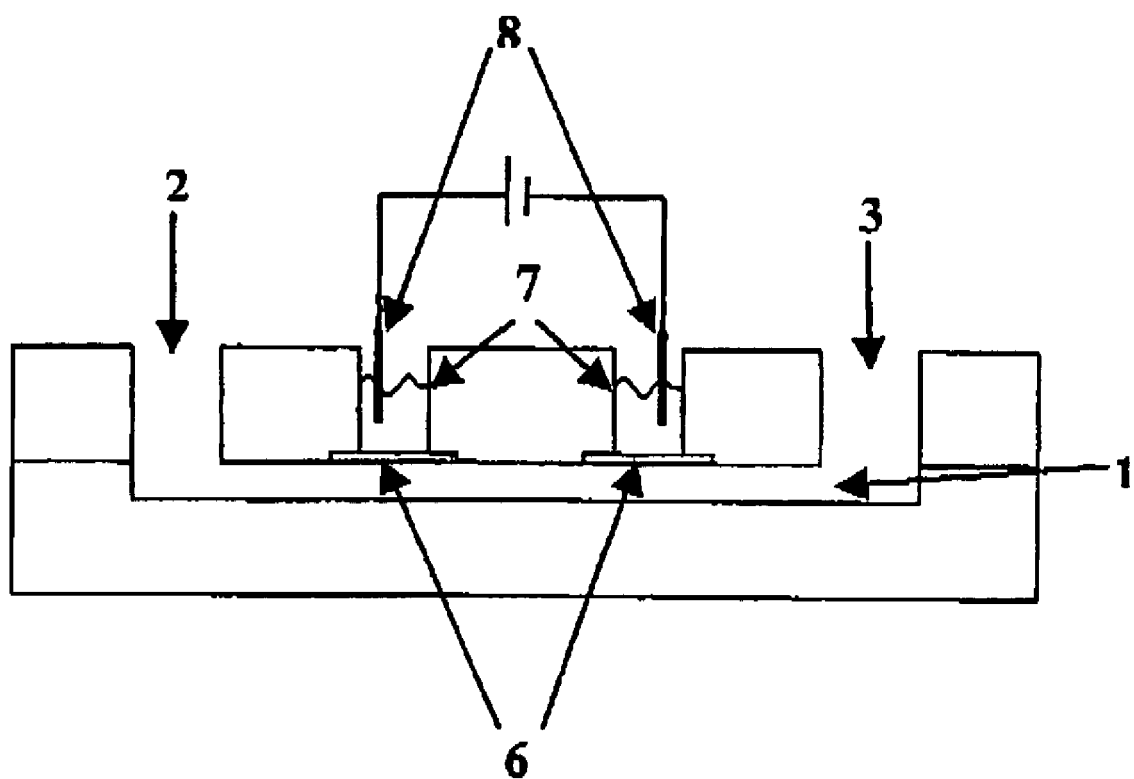
FIG. 14 illustrates a different planar design of the device according to the invention. Electrodes (8), inlet (2), outlet (3), ion-selective membranes (6), and electrolyte reservoirs (7) are shown.

Below, further designs are explained in detail;

One of the non-conducting planar structures has the inlet (2), outlet (3) and reservoirs (7) within its structure. The other structure contains the channel (1). Sheets of the ion-selective material (6) are placed between the planar structures (e.g. in a recess in the upper wafer), separating the fluidic channel from the reservoirs containing the electrodes (FIG. 14).

Figure 15:
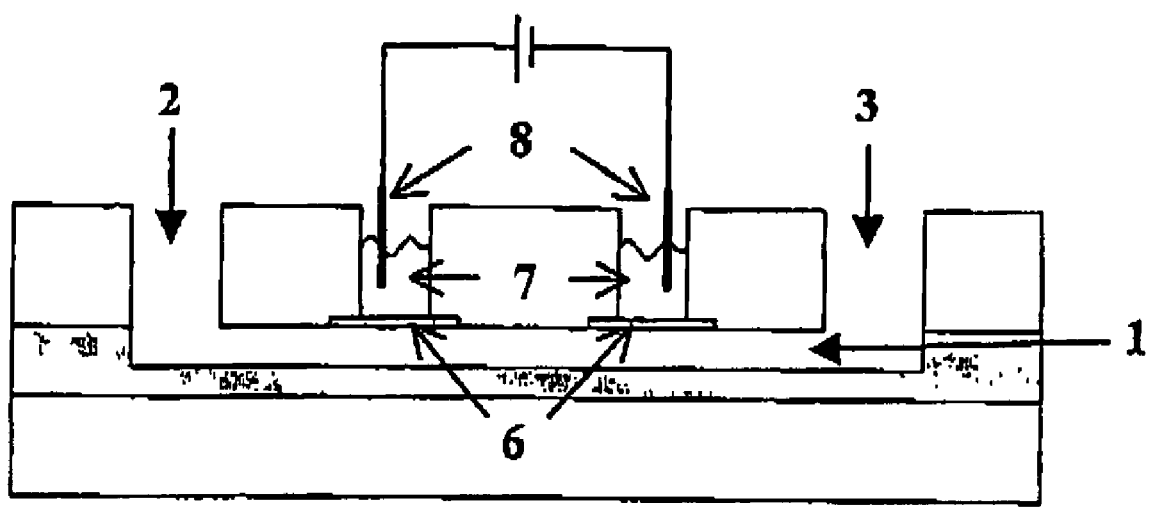
FIG. 15 illustrates a different planar design of the device according to the invention. The channel (1) is made in an intermediate layer between two planar structures. Inlet (2), outlet (3), ion-selective membranes (6), electrolyte reservoirs (7), electrodes (8) and the fluidic channel (1) are shown.

An alternative method is to structure the channel (1) in an intermediate layer, made of e.g. plastics, between the top and bottom wafer (FIG. 15).

Figure 16:
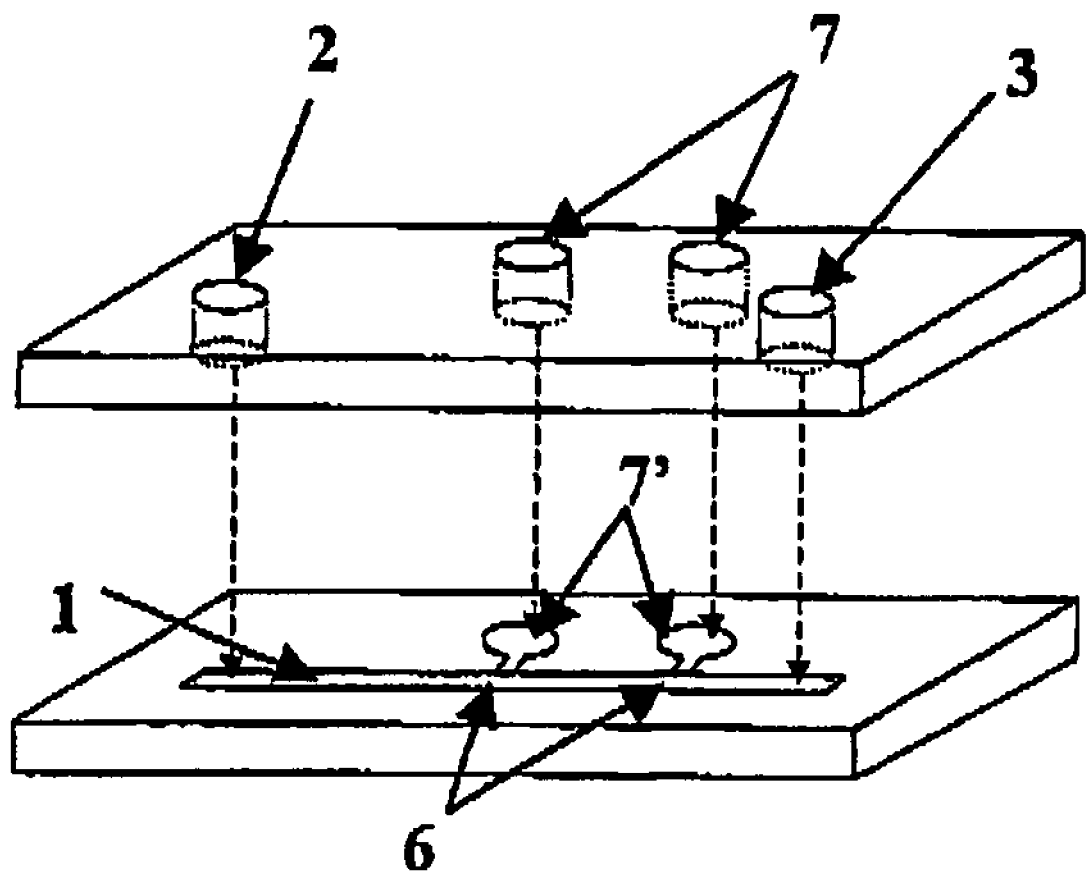
FIG. 16 illustrates a different planar design of the device according to the invention. The channel (1) and the bottom of the buffer reservoirs are built into a planar structure. The ion-selective material (6) is positioned in a way that physically separates the channel with the electrolyte reservoir (7'). The other planar structure has holes that after bonding, forms electrolyte reservoirs (7), inlet (2) and outlet (3).

In yet another design, the channel (1) and buffer reservoirs (7) for the electrodes (the later not shown) can be structured in the bottom wafer (FIG. 16). In this configuration the ion selective layer act as a membrane separating the liquid in the channel from the liquid in the reservoirs.

Figure 17:
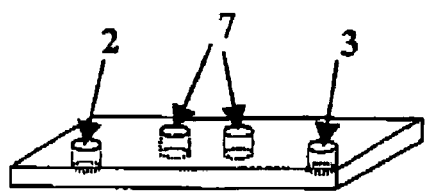
FIG. 17 illustrates a different planar design of the device according to the invention. Three planar structures which form the device (FIG. 17A). The first structure has holes which will form electrolyte reservoirs (7), inlet (2) and outlet (3). An intermediate planar structure containing holes for the electrolyte reservoirs (7') and a trench that will form the walls of the fluidic channel (1'). The holes and the trench pass through the entire depth of the planar structure. Finally, the structure that will form the bottom of the fluidic channel, having on its surface the ion-selective material which after bonding will make the electrical contact between the electrolyte reservoirs and the fluidic channel (FIG. 17B). Note that the intermediate structure has, between the trench and the electrolyte reservoir, a recess to allow the proper sealing of the fluidic channel.
Figure 17:
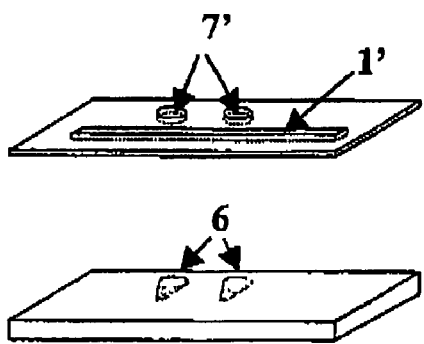
Figure 17:
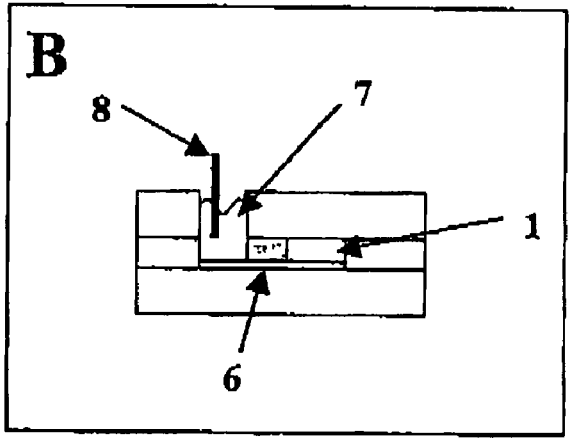

Also, the ion-selective material (6) can be placed and shaped onto the bottom of the planar structure where the channel (1) and buffer reservoirs (7) are structured into two other planar structures on top of each other (FIG. 17A). FIG. 17B shows a cross section of the electrolyte reservoir (7) of FIG. 17A The advantages of this design are that the ion-selective material is structurally independent from the wafer holes and can be modified by photolithography or dry etching.

Figure 21:
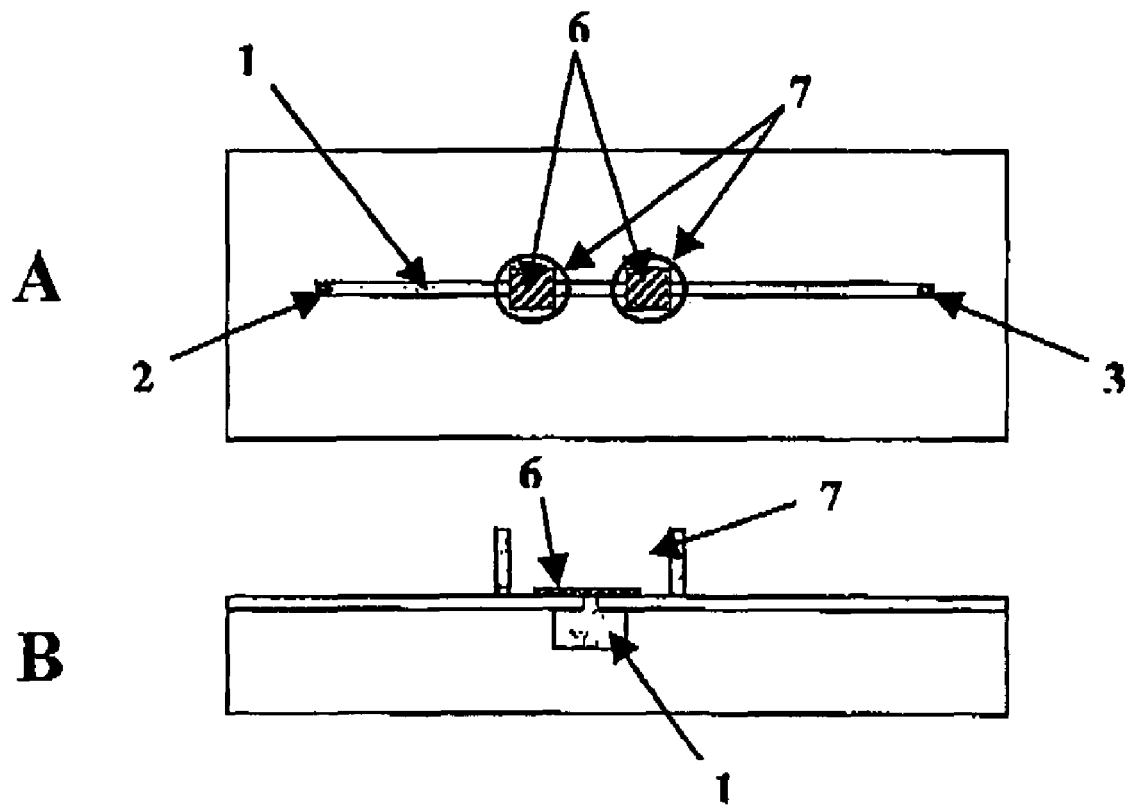
FIG. 21 illustrates a different planar design of the device according to the invention.

In yet another design (FIG. 21), the channel is built by making a trench on a planar structure and bonding on top of it a second planar structure (1). The second planar structure has holes which are covered and sealed by ion-selective material. Surrounding the electrical junction, electrolyte reservoirs can be constructed. The ion-selective material (e.g. Nafion) can be bonded or glued as a thin membrane (e.g. Nafion membrane), or patterned as liquid solution (e.g. liquid Nafion).

Construction of the capture device using planar surfaces makes it possible to have several channels in parallel, opening the possibility to run different samples in parallel using the same microchip. The microchip can be constructed in such a manner to allow individual operation of the parallel capture devices via separate conductive areas for the channels.

Figure 18:
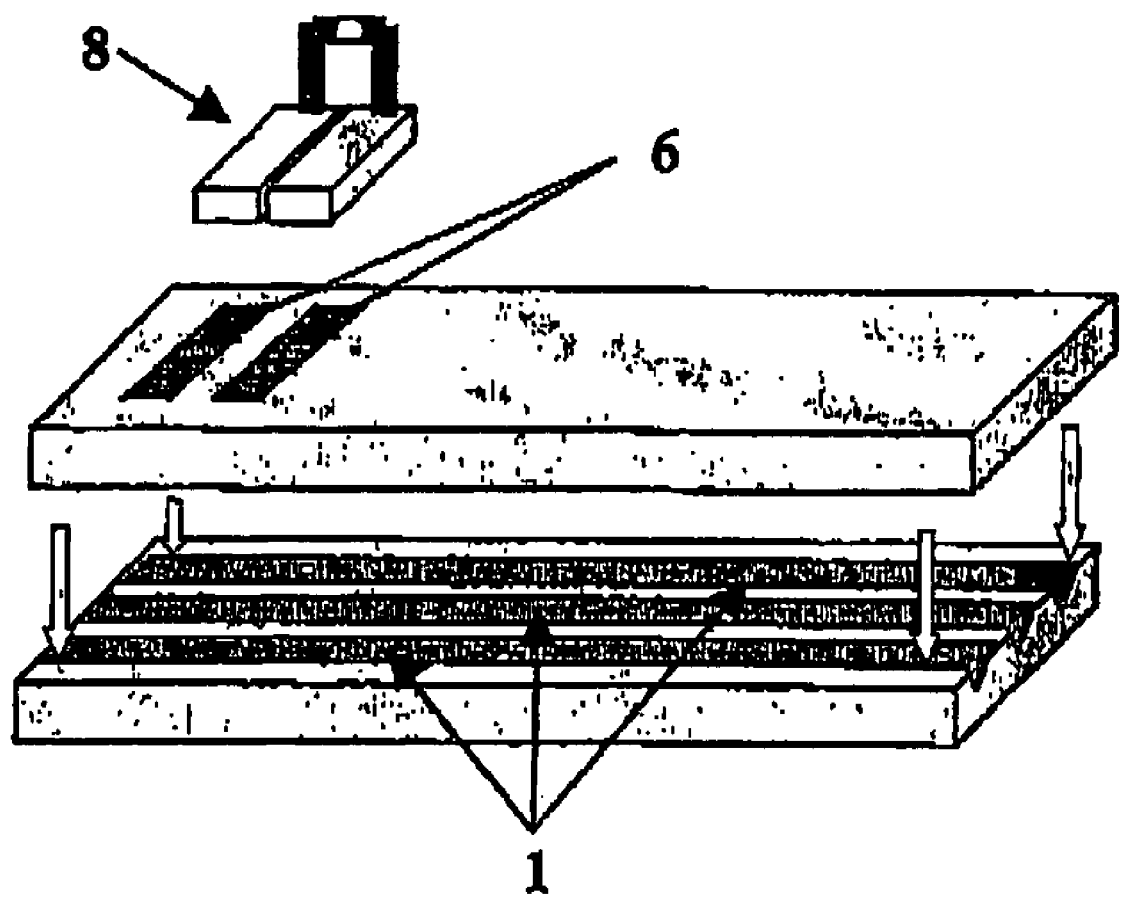
FIG. 18 illustrates a multiple channel design of the device according to the invention. The design is different from FIG. 11, having several channels in which the method according to the invention can be made in parallel.

Alternatively, a single mode operation via a single conductive strip extending to all channels can also be constructed (FIG. 18).

The hydrodynamic flow stream applied in the microfluidic device according to the invention may be produced by a pump (e.g. syringe pump, peristaltic pump, osmotic pump, diaphragm pump, solenoid pump, piezoelectric pumps or piston pump), gravity flow, gas or air pressure (using negative or positive pressure), centrifugal force or by electroosmosis. While these methods are preferred, any other method giving low flow rates (µL, nL or pL per min) can be used in the presented invention.

It is important to note that the sample processed in the capture device can be collected for further analysis or it can be monitored on-line inside the channel. In the latter case, the parallel channel approach on planar surfaces is highly suitable for multiple channel detection, e.g. using a CCD camera or confocal scanning for fluorescence detection.

Advantages

The microfluidic approach according to the invention for capturing charged biomolecules in a flow stream, has the following main advantages:

First, the device can create areas with different conductivity in an electrically continuous buffer which eliminates the necessity to inject solutions with different physico-chemical properties to achieve stacking. The stacking is used to capture certain molecules of interest traveling in a flow stream. No solid support or chemical binding is needed for this purpose.

Second, the device can be constructed simply by making two ion-selective junctions on the channel, which makes it attractive for implementation into large-scale production.

Third, the capture of charged molecules can be achieved by adjustment of the voltage and/or flow rate, without the necessity of a physical change of the system. For example, under appropriate pH-conditions, DNA, proteins and peptides are charged and the change of voltage and/or flow rate can allow adequate retention (even though the net charge and physico-chemical properties of these molecules are diverse).

Fourth, the stacking area can be used to capture particular ions in a preparatory fashion and can be further used as a mixer, incubator or reaction chamber.

Fifth, as the electrodes are situated outside the channel, bubbles or other products generated by electrolysis (e.g. oxygen, OH or $H^+$ ions or products from oxidation or reduction reactions) are produced in the electrode buffer reservoirs and not inside the channel. Disturbances of the current by bubbles, changes of pH, or sample modifications by direct contact with the electrodes are avoided.

Particular Non-Limiting Applications

The device according to the invention can be used for on-line sample desalting for DNA sequencing by capillary electrophoresis (CE). The device can be used to capture DNA fragments in a flow stream, concentrating, desalting and removing leftover PCR products for subsequent on-line injection into a CE device with laser induced fluorescence detection (CE-LIF) for DNA sequence analysis. The on-line device connected to CE-LIF is capable to improve the sensitivity and resolution in DNA sequence analysis. One example DNA capture is shown in Example 3.

Figure 8:
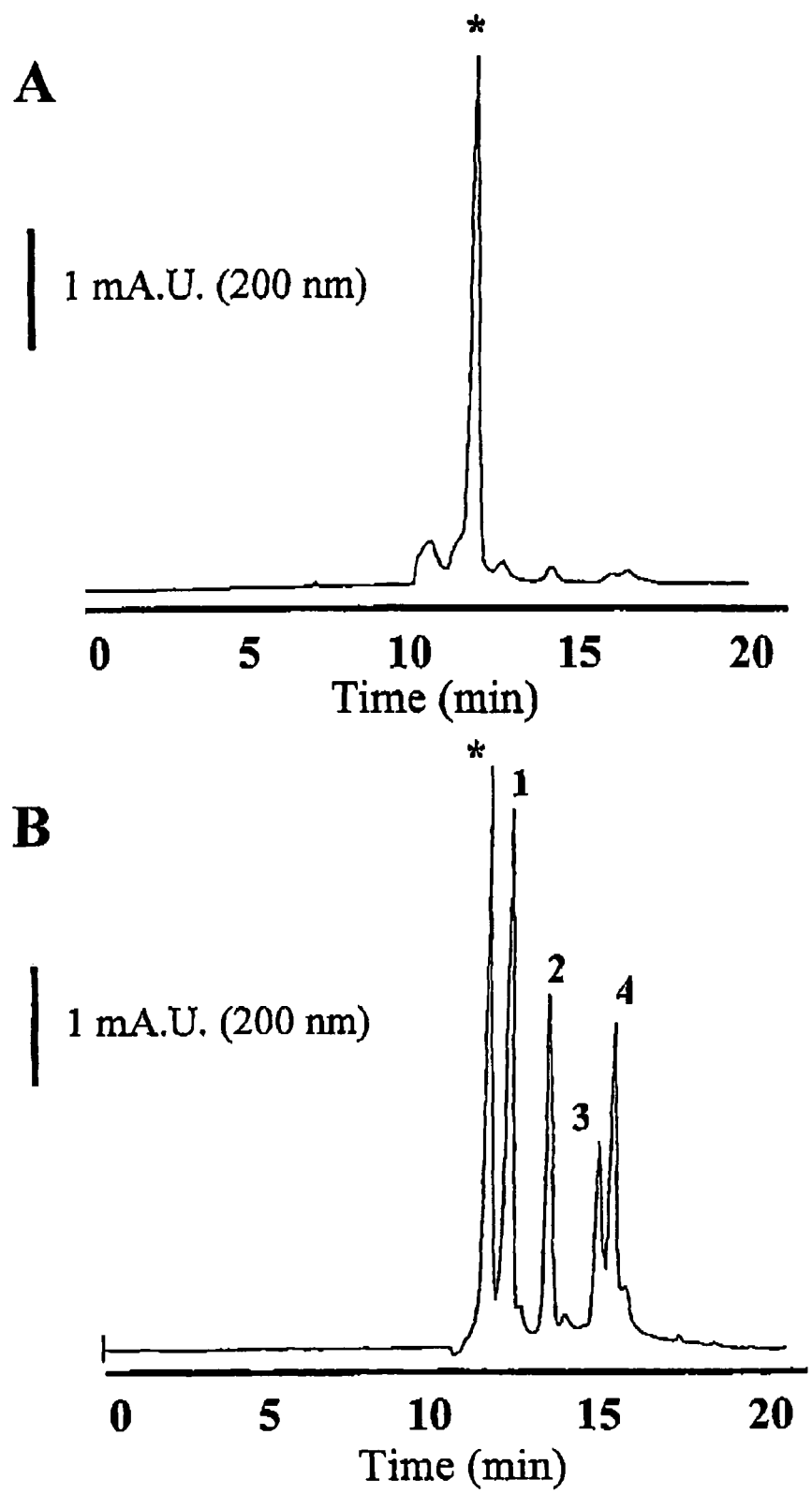
FIG. 8. Electropherograms obtained from model proteins separated on a CE system using a conventional gravity hydrodynamic flow injection method (A) and the capture device (B). For both experiments, 3 µg/ml of each protein was dissolved in 10 mM Tris-HC1, pH 8.0. (1) bovine carbonic anhydrase, (2) α-lactalbumin, (3) β-lactoglobulin A, (4) 13-Lactoglobulin B and (*) Tris buffer peak. For the hydrodynamic injection (A), the sample vial was elevated 14 cm above the cathode vial for 8 s. Capture-device preconcentration (B) was performed for 60 min at 0.3 µl/min and 187 V/cm.

The device according to the invention can be used as a fluidic preconcentrator device for capillary electrophoresis analysis of proteins. The system is able to capture proteins for off-line preconcentration before CE. Different proteins have been tested, demonstrating that several microliters of solution containing proteins with different charges and molecular weights can be concentrated into a few nanoliters and subsequently injected into the system. A preconcentration factor of up to 40 has been achieved (FIG. 8).

Figure 9:
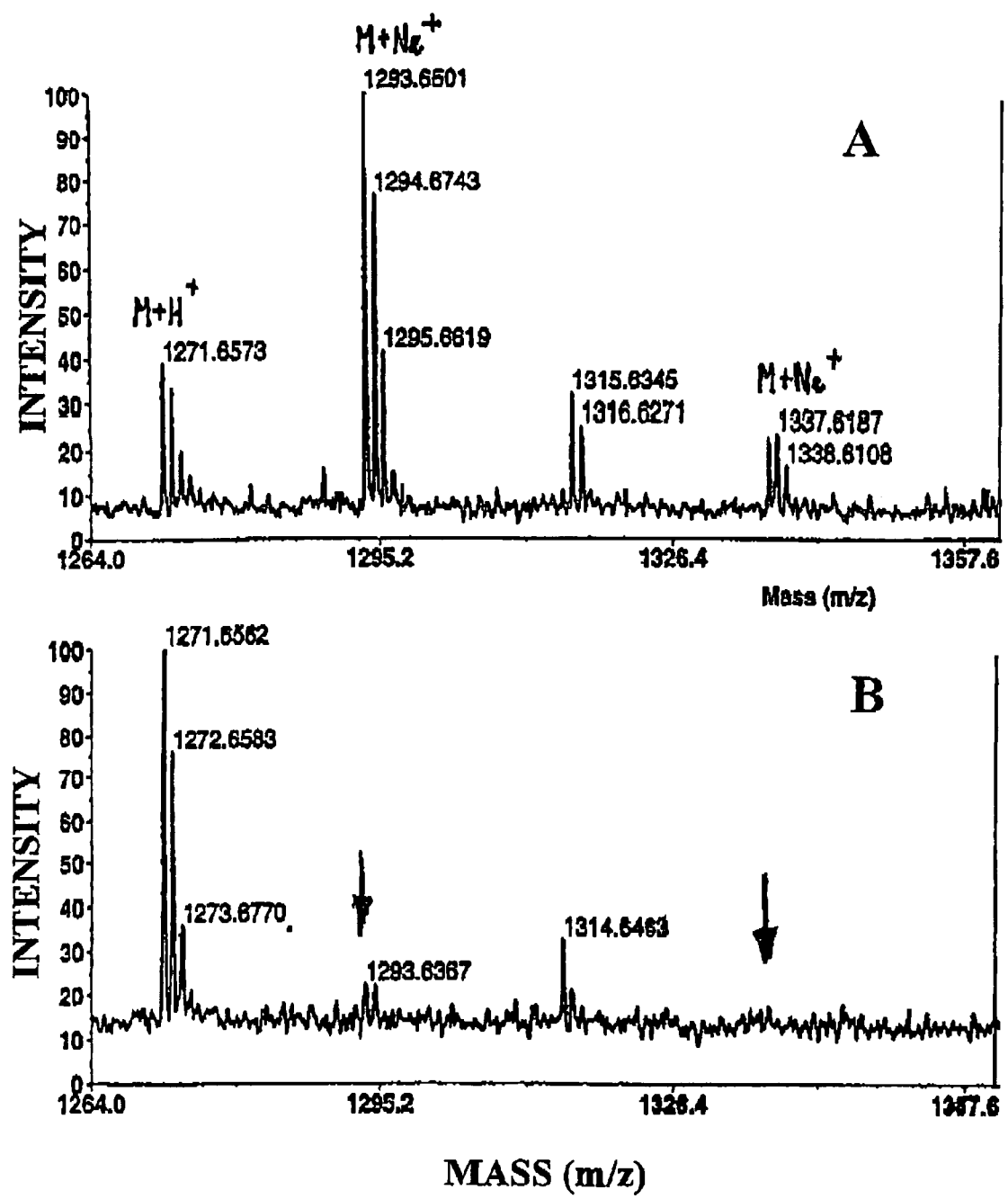
FIG. 9. MALDI-TOF spectra of myoglobin tryptic digest (0.1 pmol/µL) containing 50 mM phosphate buffer, and 40 mM NaCl. (A) crude sample without desalting, and (B) sample desalted using the microfluidic electrocapture device. $M+Na^+$ indicates peptide peaks contaminated with sodium ions. Arrows point to the absence of those peaks after desalting using the device according to the invention.

The device according to the invention can be used for sample cleanup for analysis of peptides by matrix-assisted laser desorption/ionization mass spectrometry (MALDI-MS). Although MALDI-MS has a relatively high tolerance to contaminants, sample purification is necessary to achieve maximum sensitivity and high quality spectra for accurate mass determination and efficient database searches. The presence of salts, detergents and other interfering molecules decreases the overall signal intensity and increases spectra complexity due to introduction of adduct peaks (e.g. alkali metal adducts). The device is able to capture peptides (tryptic fragments) and proteins in a flow stream for desalting, preconcentrating and detergent removal (e.g. CHAPS) resulting in high quality MALDI-MS spectra for tryptic peptide mass mapping and protein identification (FIG. 9).

The device according to the invention can be used as a reaction chamber to carry out single-step or multi-step microreactions. The approach opens up a new strategy to manipulate diverse molecules without the use of a solid support and perform on-line reactions in a single fluidic channel. A target protein is captured, after which another medium is injected into the system. The second medium carries enzymes and/or other reagents, which are brought into contact with the target protein and react. The reaction can occur in two manners; reactants can be co-captured in the same spot as the target protein and react (e.g. if the second medium contains an enzyme (e.g. trypsin)), or they can pass through the capture zone and react by molecular collisions with the electro-immobilized protein (e.g. if the second medium contains molecules with different electrophoretic behavior than the capture analyte (e.g. dithiothreitol or iodoacetamide)). Experiments have demonstrated that it is possible to first capture a protein, and then inject an enzyme that is captured in the same spot as the substrate protein. Since the target protein and the enzyme are brought into close contact, the present invention serves as a microfluidic digestion chamber of a few nanoliters volume. After incubation, the proteolytic products are released and analyzed for example by MALDI-MS.

Figure 10:
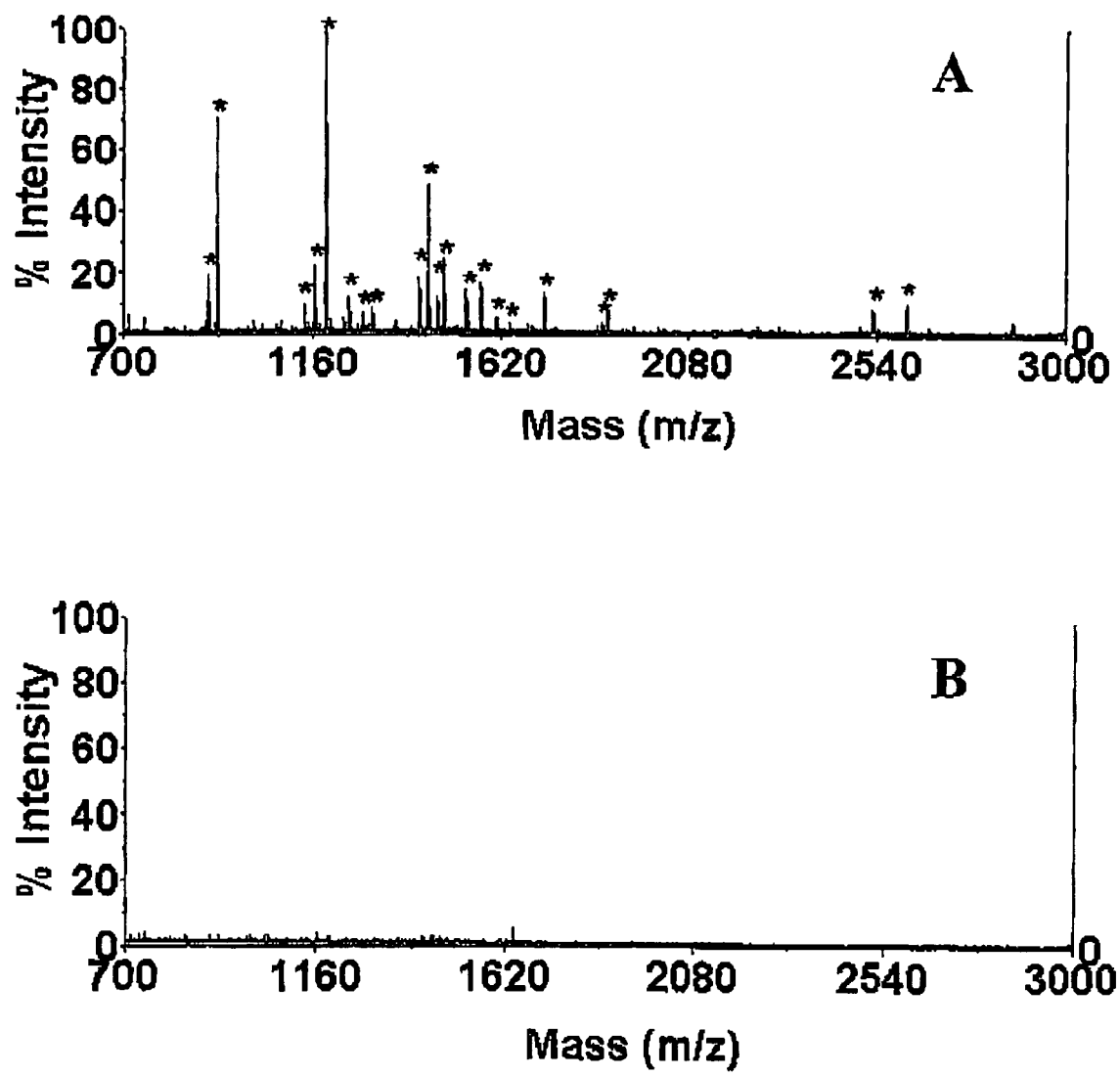
FIG. 10. MALDI-TOF spectra of single (A) and multistep microreactions (C). In (A), 1 pmol of myoglobin was captured, followed by the injection and capture of 10 pmol of trypsin. Proteins were dissolved in 30 mM Tris buffer, pH 8.0, in 50% acetonitrile. After 30 min of incubation time, the power supply was turned off and products were directly spotted onto the MALDI plate and analyzed. (A) Successful capture and digestion of myoglobin, using a flow rate of 0.3 µL/ml and 190 Went. (B) Blank experiment, using the same experimental conditions but without the application of voltage. In (C), disulfide bond reduction with dithiothreitol, followed by carbamidomethylation with iodoacetamide, and subsequent proteolytic digestion with trypsin is shown.
Figure 10C:
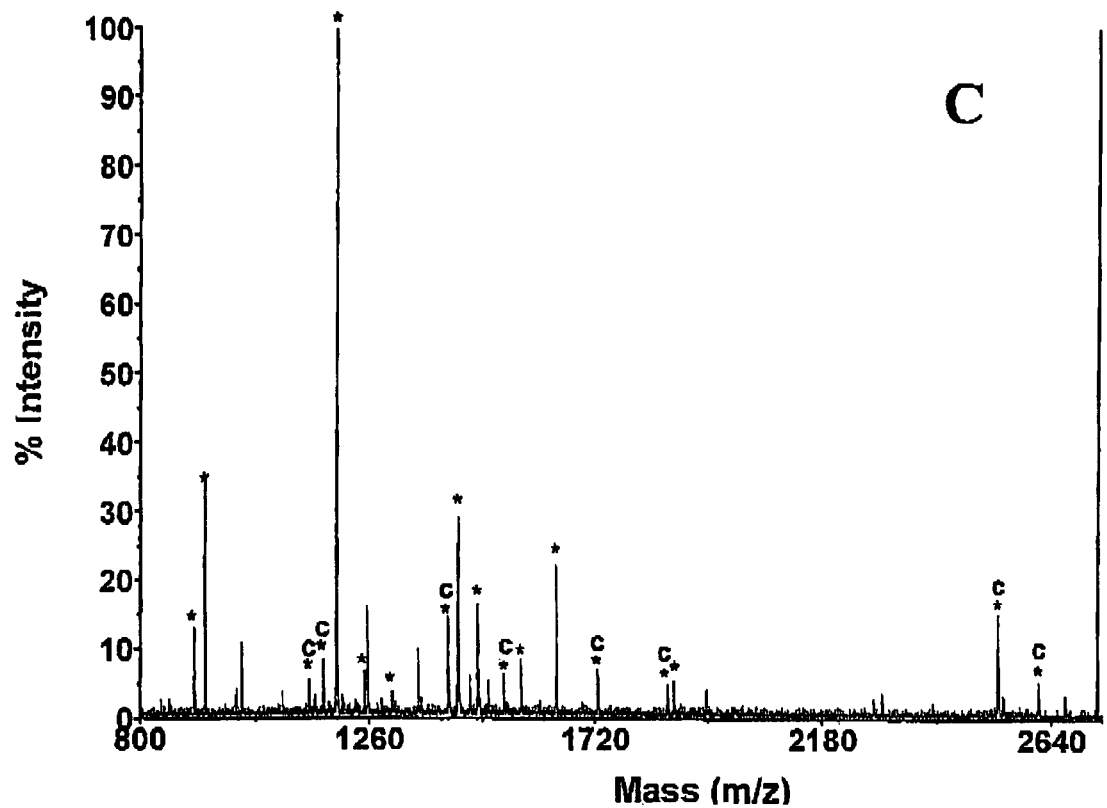

Experimental data show that it is possible to capture a target protein (e.g. bovine serum albumin or myoglobin) followed by the injection and co-capture of a proteolytic enzyme (trypsin). After 30 min incubation, the digestion products were successfully recovered for MALDI-MS analysis, demonstrating the feasibility to use this system for on-line microreactions (FIGS. 10A and 10B). Furthermore, experimental data show that it is possible to perform multi-step reactions as on-line reduction, alkylation and trypsin digestion of proteins (FIG. 10C).

EXAMPLES AND ADDITIONAL DATA

The invention will now be illustrated by the following non-limiting examples or evidences.

Example 1

Experimental Evidence for the Membrane-Based Stacking Principle

In order to validate the theoretical principle, a device that contains all desirable characteristics outlined in the theoretical part was built and tested.

The system consists of a micrometer size flow channel made of PEEK tubing, which has two gap junctions covered by a cation-selective conductive membrane. The junction zones are placed into separate electrode buffer chambers. The PEEK tubing serves as electrophoretic channel and the cation-selective conductive membrane will not permit the exchange of anions between the buffer chambers and the fluidic channel. A syringe pump connected to the channel produces a flow stream (FIG. 3). Theoretically, having the anode at the upstream junction, negatively charged molecules will be attracted towards the upstream electrode and trapped there by the capture device.

The electrical junctions are made of Nafion tubing. Nafion is a poly(tetrafluoroethylene) polymer that contains sulfonic and carboxylic acid groups. The polymer is therefore highly negatively charged and its pore structure makes it possible to use the membrane as a cation-selective barrier. In practice, the membrane is only permeable to small cations (e.g. sodium or protons) and the small pore size of the membrane (about 10 Angstroms) will prevent the passage of large molecules into the electrode chambers (e.g. DNA, proteins and peptides).

The existence of two zones of different electric field strength was confirmed by direct measurements of its value at the upstream and downstream regions. As seen in Table 1, a lower electric field zone is situated upstream and a higher electric field zone is situated downstream.

TABLE 1

| Flow rate µL/min | Flow velocity cm/s | Upstream electric field[1] V/cm | Downstream electric field[2] V/cm | Ratio Flow velocity/ upstream electric $cm^2V^{-1}s^{-1}$ | Theoretical electric field of the ion-concentrated area V/cm |
|---|---|---|---|---|---|
| 0.1 | 0.013 | 17 | 320 | 7.60E−04 | 16 |
| 0.2 | 0.026 | 32 | 276 | 8.10E−04 | 23 |
| 0.3 | 0.039 | 52 | 247 | 7.50E−04 | 49 |
| 0.5 | 0.052 | 67 | 185 | 7.70E−0 | 66 |
| 0.5 | 0.085 | 79 | 147 | 8.20E−04 | 82 |
| 0.7 | 0.091 | 97 | 104 | 9.40E−04 | 115 |
| 1 | 0.131 | 100 | 99 | 1.30E−03 | 166 |

TABLE 1-continued

| Flow rate μL/min | Flow velocity cm/s | Upstream electric field[1] V/cm | Downstream electric field[2] V/cm | Ratio Flow velocity/ upstream electric $cm^2V^{-1}s^{-1}$ | Theoretical electric field of the ion-concentrated area V/cm |
|---|---|---|---|---|---|
| 2 | 0.262 | 99 | 98 | 2.60E−03 | 331 |
| 3 | 0.393 | 100 | 99 | 3.60E−03 | 497 |

[1] Electric field values of upstream and downstream regions under different flow rates. In order to measure the electric field of the upstream and downstream regions, the design of the capture device was modified. The system now has five electric junctions, where the electric field is applied between the first and fifth junction. The electrical junctions situated between the first and fifth junction are electrically floating, and are utilized to measure the electric field along the fluidic channel. Five openings were made with a razor blade to PEEK tubing (125-μm i.d., 512-μm o.d.) at a distance of 0.5-cm from each other. Each gap was covered with an individual piece of Nafion tubing (360-μm i.d., 510-μm o.d.), and placed into separate electrode chambers, made of 0.5 mL plastic micro-centrifuge tubes, that were glued in place with epoxy. The electrode chambers were filled with 100 mM Tris-HCl, pH 8.0. A syringe pump connected to the device provides the continuous injection of a 50 mM Tris-HCl buffer pH 8.0. An electric potential of 400 V was applied between the first and the and fifth junction, in a manner that the anode was situated upstream and cathode downstream.
[2] Electric field value between the first electrical junction (anode gap) and the next situated 0.5 cm downstream.
Electric field between the last electrical junction (cathode gap) and the one situated 0.5 cm upstream.

By using Equation 1, and the electric field values at a flow rate of 0.2 μL/min (Table 1), the following conclusion can be made. In the present device, a flow rate of 0.2 μL/min produces a flow stream with a linear velocity of 0.026 cm/s. Therefore, in order to capture molecules traveling in a flow stream, the resulting electrophoretic velocity created by the electric field must counteract the velocity of the flow. Thus, the electrophoretic velocity must be of equal or higher value (and opposed direction) than the linear velocity of the flow stream. Therefore, ions with electrophoretic velocities lower than the linear velocity of the flow stream will be swept out from the system. By using Equation 1, we can calculate the minimum of electrophoretic mobility ($\mu_{min}$) that a molecule must have in order to produce an electrophoretic velocity high enough to comply with the conditions of capture at any given electric field and flow rate values, thus;

$$\mu_{min} = v_h/E \quad \text{Equation 4}$$

$v_h$ = linear velocity of the flow
$\mu_{min}$ = minimum electrophoretic mobility
E = electric field strength As seen in Table 1, at a flow rate of 0.2 μL/min (linear velocity of the flow stream of 0.026 cm/s) the electric field upstream is 32 V/cm. By using Equation 4, we can establish that under this electric field only molecules with a μ-value higher than $8.1 \times 10^{-4}$ $cm^2V^{-1}s^{-1}$ will produce an electrophoretic velocity high enough to counteract the velocity of the flow. Thus, at the upstream region, molecules with a μ-xalue lower than $8.1 \times 10^{-4}$ $cm^2V^-s^{-1}$ will be swept towards the downstream region of higher electric field. On the other hand, at the same flow rate, the electric field downstream is 276 V/cm. By using the same reasoning as above and Equation 4, we can establish that at the downstream region the minimum μ-value that a molecule can have in order to be captured is $9.42 \times 10^{-5}$ $cm^2v^{-1}s^{-1}$. Therefore, in this region, molecules with μ-values higher than $9.42 \times 10^{-5}$ $cm^2v^-s^{-1}$ will move upstream, and molecules with lower μ-values will be swept out from the system, Considering $\mu_{min}$ values of the upstream and downstream regions, molecules with μ-values lower than $8.1 \times 10^{-4}$ $cm^2V^{-1}s^{-1}$ and higher than $9.42 \times 10^{-5}$ $cm^2v^{-1}s^{-1}$ will be captured or "trapped" between these regions, because their electrophoretic velocities in the downstream region are high enough to move the molecules upstream but not sufficient to make them enter into the upstream region.

Figure 5:
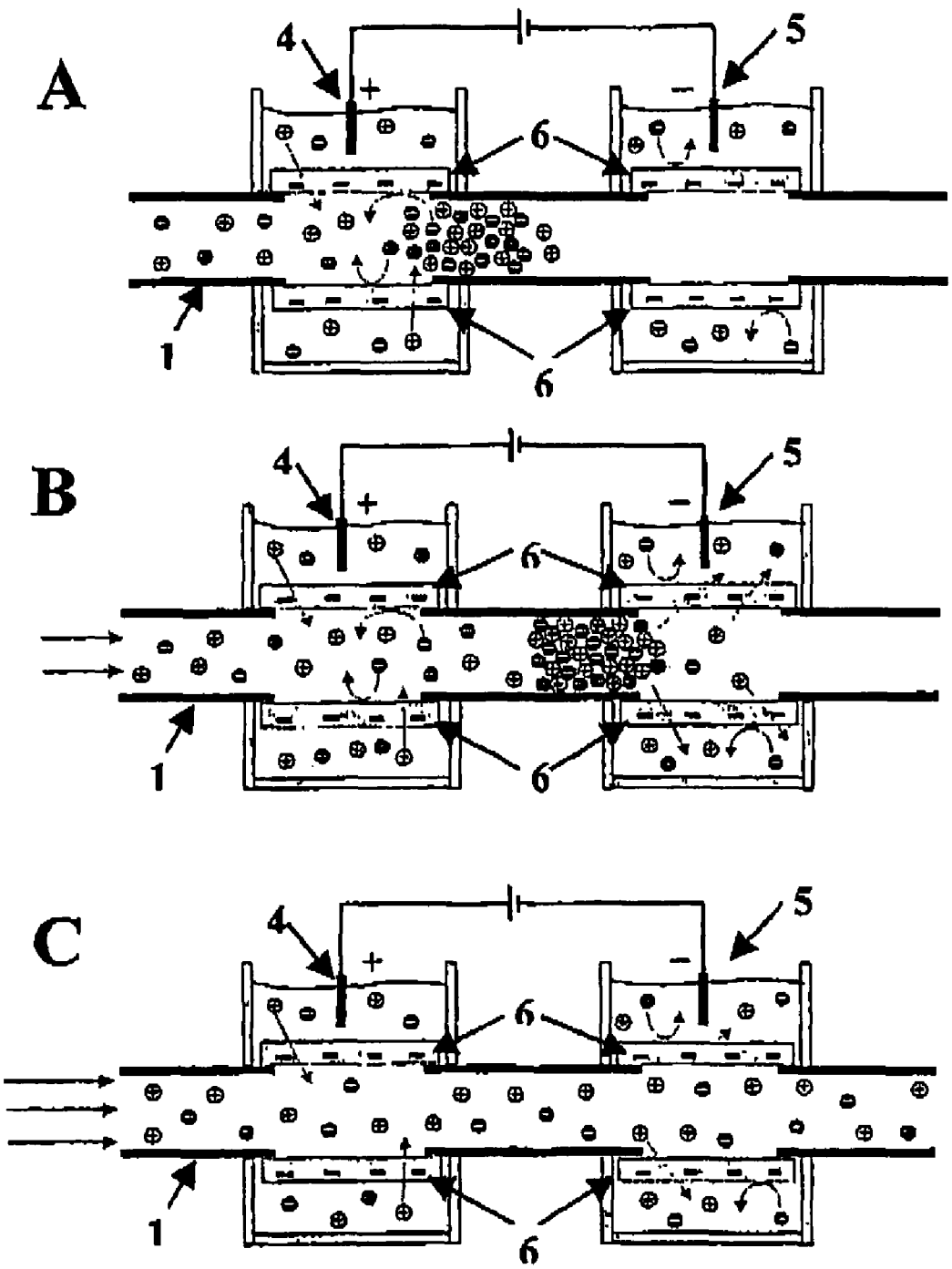
FIG. 5. Schematic diagram of the capture device electrical behavior under different flow conditions. In static (A), moderate (B) and high flow rate (C). Black and white spheres represent anions and cations, respectively. As is explained in detail in the text, the ion-depletion zone formed by the cation-selective properties of Nafion, creates a membrane-based stacking effect that is responsible for the current behavior at low flow rates.

Similar reasoning can be made for flow rates of 0.5 μL/min, 0.4 μL/min, 0.3 μL/min and 0.1 μL/min. As seen in Table 1, differences in the electric field values between the upstream and downstream regions vanished at flow rates higher than 0.5 μL/min., This effect is because, at these flow rates, the velocity of the flow stream is too high to capture any ion present in the fluidic channel, and therefore creating a homogeneous electric field. This effect is represented in FIG. 5C.

It should be noted that in the experiments presented, the anion in higher concentration and responsible for creating the high ionic strength area is the chloride ion (Cl). Since at the capture, chloride ions have the same electrophoretic velocity as the linear velocity of the flow stream ($v_e = v_h$), the electric field strength at the place where these ions are located can be calculated from rearrangement of Equation 1. Thus during capture the chloride ions will be under an electric field ($E_{Cl}$) given by;

$$E_{Cl} = v_h \mu_{Cl} \quad \text{Equation 5}$$

$v_h$ = flow velocity
μ = electrophoretic mobility
$E_{Cl}$ = electric field strength where chloride ions are located The value of μ for the chloride ion is $7.91 \times 10^{-4}$ $cm^2V^{-1}s^{-1}$. The theoretical values for electric field strength at the place where chloride ions are in equilibrium with the hydrodynamic flow are shown in Table 1. From Table 1, it can be concluded that the chloride zone is situated at the upstream region since the theoretical electric field values match with the experimental values for flow rates below 0.7 μL/min. In addition, the ratio between the linear velocity of the flow and the corresponding upstream electric field strength between 0.1 μL/min and 0.5 μL/min are similar to the μ value of the chloride ion ($7.91 \times 10^{-4}$ $cm^2V^{-1}s^{-1}$), supporting the conclusion that the chloride ion is responsible for the low electric field in the upstream region.

From this fact, the following conclusions can be made;

First, from Equation 5 we can conclude that ions with higher mobility will produce a lower electric field at the upstream region, thus increasing the range of molecules that can be captured by the present invention.

Second, if ions with different μ-values are present in the flow stream, and are captured by the present invention, they will be located (or captured in the flow stream) at different positions along the channel according to the resultant electric field (as described for chloride ions), always with the ion with a higher μ-value situated upstream to an ion with a lower μ-value. These ions will be located under a local electric field related to its own $v_h/\mu$ ratio.

Third, even though captured molecules with different μ-values are located along the fluidic channel at different places according to the electric field generated by the ratio between the linear velocity of the flow and their particular μ-values, two molecules with different la-values can be located at the same position by creating a zone where the linear velocity of the flow stream is lower than in the rest of the fluidic channel. This zone with lower flow velocity should be located downstream from the area of lower electric field. This means that the area of high ionic strength and low electric field should be located in the portion of the channel that has a higher flow velocity. Thus, all the ions that cannot enter the zone of high flow velocity due to the low electric field, but have an electrophoretic velocity high enough in the area with a lower flow velocity to move upstream towards the zone of high flow velocity, will be located at the boundary between said areas.

As the electrical current reflects the overall behavior of ions in the system, current versus flow rate plots were analyzed and compared to the theoretical model, and visual observations were made.

Figure 4:
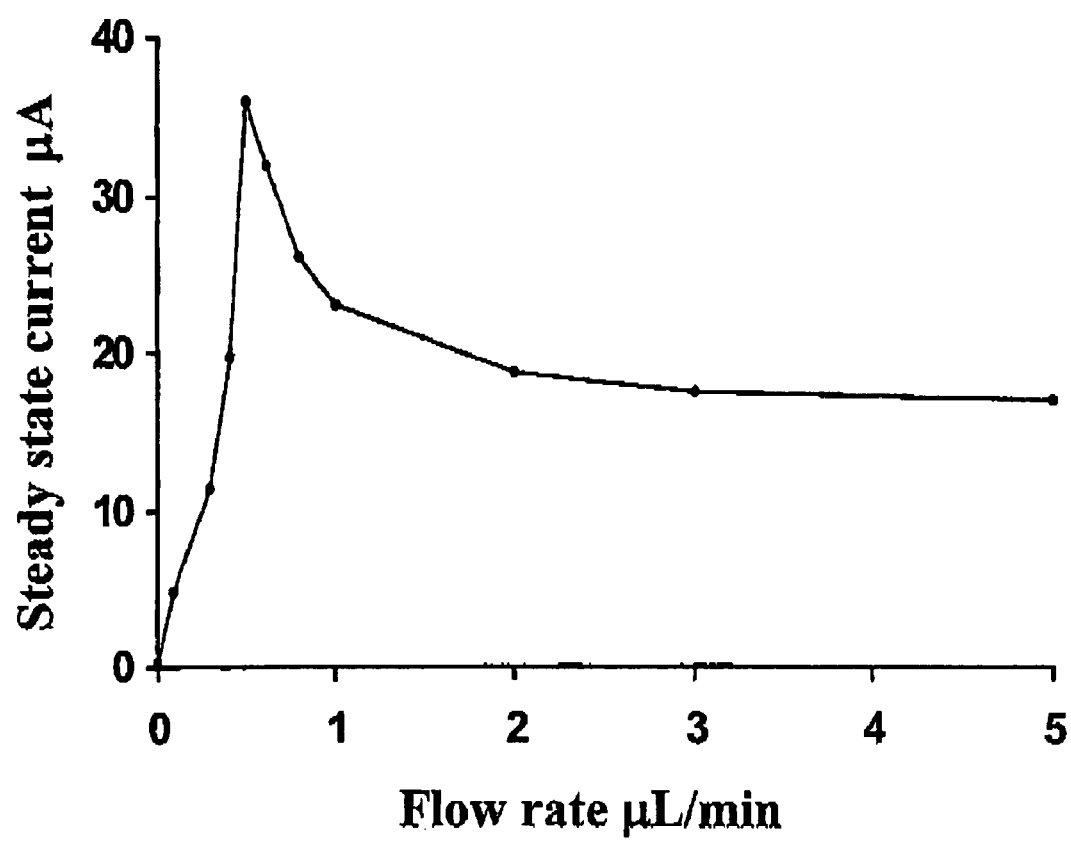
FIG. 4. Capture device current versus flow rate. Current was measured after 15 miry of operation at flow rates between 0 and 5 µl/min, using a solution of 10 mM Tris-HCl, pH 8.0, and 300 V (187 V/cm) between the cation selective membranes.
Figure 6:
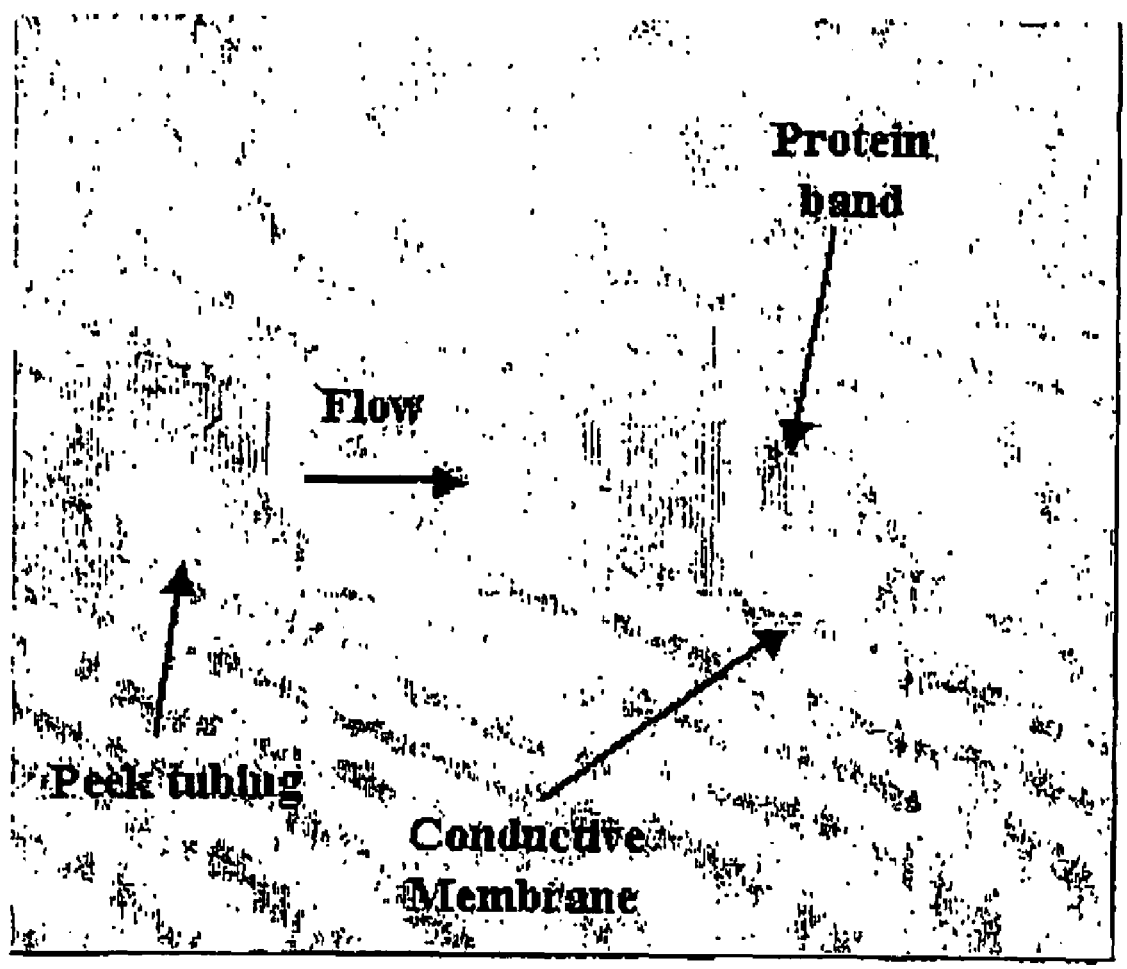
FIG. 6. Image of the downstream cathode junction during capture device operation. A solution of 0.5 mg/ml horse muscle myoglobin, 0.25 mg/ml human hemoglobin A, and 0.4 mg/ml bovine serum albumin, in 10 mM Tris-HCl, pH 8.0, was injected into the system and captured at a flow rate of 0.4 µl/min and 300 V (187 V/cm) between the gaps. A few seconds after application of the capture voltage, a concentrated protein band could be seen.

From the experimental data shown in FIG. 4 and FIG. 6, the following conclusions can be made:

In the absence of hydrodynamic flow, the system develops a high electrical resistance, decreasing the current to almost zero (FIG. 4), independent of the magnitude of the applied voltage. As the electrolyte solution in the electrode buffer chambers cannot be responsible for this phenomenon (it is a continuous solution), the resulting high electrical resistance must be related to some phenomenon taking place inside the microfluidic device, Since the membrane has good conductivity properties and only ions are responsible for the charge transport (current), an altered resistance must be related to the behavior of ions inside the system.

Due to the cation-selective characteristics of the Nafion membrane, we can assume that anions are being accumulated in the system creating a discontinuous zone in the buffer. Since the anode is situated at the upstream junction, it can be anticipated that the high-concentrate anion zone is close to the anodic membrane, while the low-concentrate ion zone is situated somewhere towards the cathode. In this situation, less cations pass the membrane and enter the channel from the anode buffer chamber than are leaving the channel to enter the cathode buffer chamber. This phenomenon can be attributed to the fact that cations situated close to the cathode gap are under higher electric field than at the anode gap which means that the flux of cations from the fluidic channel to the cathode buffer chamber will be faster than the flux of cations from the anode buffer chamber into the fluidic channel. Due to the fact that the cation outflux is higher than its influx, the fluidic channel rapidly runs out of cations (FIG. 5A), and since only cations are responsible for the charge transport (electrical current) between the fluidic channel and the electrode buffer chambers, the phenomenon explained above should be responsible for the high electrical resistance developed by the system, This is also in agreement with the overall current versus time plot in the absence of hydrodynamic flow, where a high peak current value is observed during the first few seconds of operation followed by a sharp drop in the current to reach values close to zero. The current peak corresponds to the movement of cations in and out of the channel until the high-concentrate anion zone is created. After this, the imbalance between the outflux and influx of cations creates the depletion zone which in turns decreases the current values to almost zero.

Under low flow rates (0.1 to 0.5 μL/min), the current value starts to increase until a maximum at 0.5 μL/min, after which the value decreases until a constant current at flow rates higher than 2 μL/min (FIG. 4). As the flow rate increases, the anion-concentrate zone is swept downstream towards the cathode junction gap, decreasing the length of the low-conductivity area and therefore decreasing the overall resistance of the system which in turn, increases the current (FIG. 5B).

Example 2

Capture of Proteins

To compare the movement of slow anions with the theoretical model by visual observations, colored proteins such as myoglobin and hemoglobin were captured in the device (FIG. 6).

The protein band can be moved along the channel by changing the voltage or flow rate. For a given voltage, the protein band is situated more upstream if the flow rate is decreased (with lower overall current value) while the band is swept downstream if the flow rate is increased, resulting in higher overall current value. The maximum flow rate when the protein band is no longer captured was found to be 0.4 μL/min for an electric field of 187 V/cm (FIG. 6). This is in general agreement with the maximum current value, at 0.5 μL/min (FIG. 4). From these data, it can be assumed that at 0.4 μL/min the low conductive zone, which produces the stacking effect, is as short as possible to still achieve the capture effect, and at higher flow rates the band is swept out from the system. After this point, the high conductivity zone totally replaces the low conductivity area (at 0.5 μL/min) resulting in the highest current value (FIG. 4). An increase in the flow rate above this level, decreases the length of the high conductivity area, which in turn decreases the current value until the high conductivity area is completely swept out from the system. Under these conditions, not even high velocity anions can be captured in the system (>2 μL/min), resulting in a steady-state current in the system, independent of the flow rate (FIG. 5C).

With the theoretical model proposed and the empirical data presented, we conclude that it is possible to build a device generating a discontinuous zone in a continuous buffer that allows stacking and retention of charged molecules, such as DNA, proteins and peptides in a flow stream.

Example 3

Capture of DNA

Figure 7:
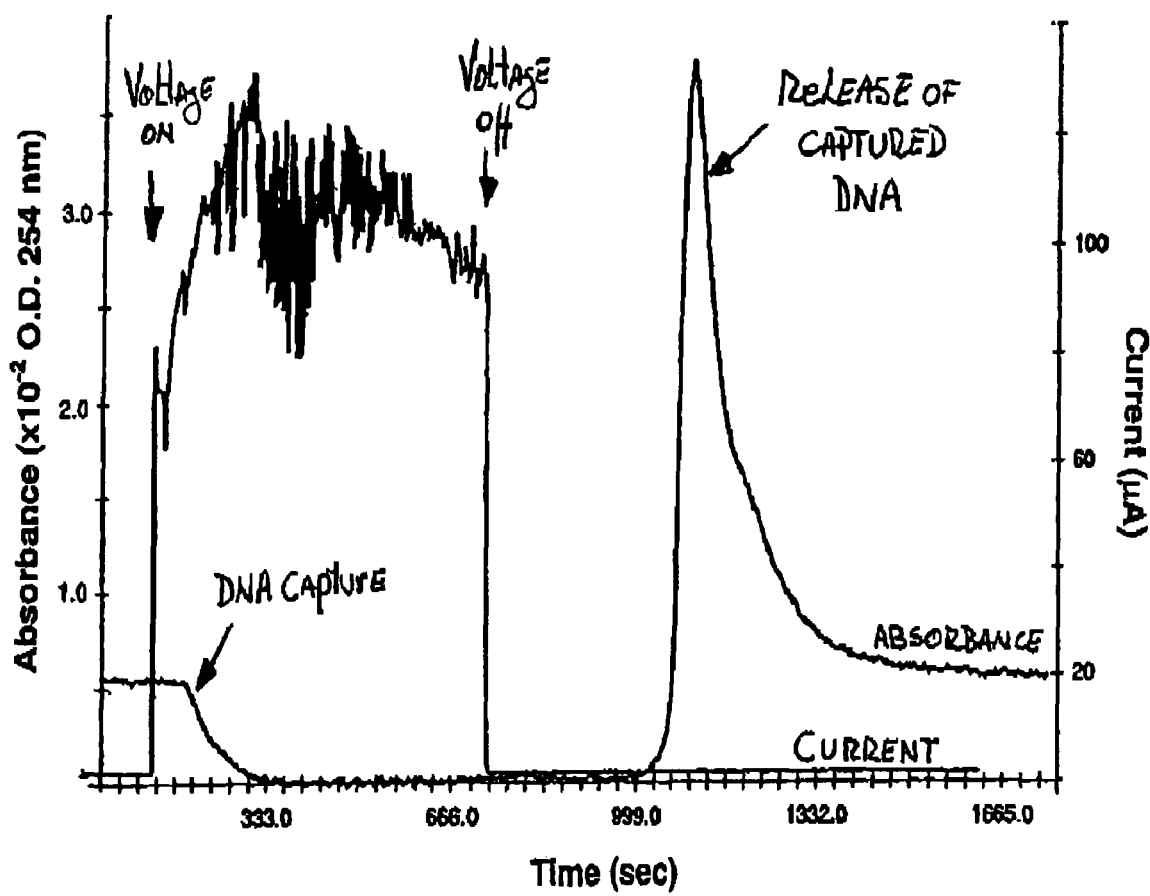
FIG. 7. Capture-device current and capture-release profiles during operation. The device described in Section 2.3 was used to capture lambda-DNA digested with Hind III restriction enzyme. A solution of 0.8 µg/4 lambda-DNA/Hind 111 digest (53.5 mM Tris-HC1, 5 mM $MgCl_2$, 1.25 mM NaCl and 0.1 mM EDTA at pH 8.0) was injected continuously at 0.3 'IL/min into the device giving a steady level of DNA passing through the detector. After the application of the voltage (153 V/cm), a decrease in the signal indicates that DNA is being captured by the system. Shortly after turning the voltage off, a single peak of captured DNA was observed at the detector.

In order to optimize the voltage and flow rate values, a solution of DNA was injected continuously into the device. An UV absorbance detector was positioned at the outlet of the device. Under this configuration, a decrease of the absorbance values represents that DNA is being captured. For optimization, different values of voltage were tested using a constant flow rate. A successful capture of DNA can be seen in FIG. 7. A decrease in the UV absorption at the detector shows that DNA is being captured. As soon as the electric field is turned off, a sharp band of the released DNA is observed.

Although the invention has been described with reference to specific embodiments, these descriptions are not meant to be construed in a limiting sense. Various modifications of the disclosed embodiments, as well as alternative embodiments of the invention, will become apparent to persons skilled in the art upon reference to the description of the invention. It should be appreciated by those skilled in the art that the conception and the specific embodiment disclosed might be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore contemplated that the claims will cover any such modifications or embodiments that fall within the true scope of the invention.

What is claimed is:

1. A method for capturing charged molecules of interest traveling in an electrolyte flowing stream through an electrically non-conductive channel comprising at least one anode and at least one cathode individually separated from said channel but in electrical contact with said flow stream by a conductive semi-permeable membrane, said method comprising the steps of:

permitting via said membrane the selective passage of certain charged ions or molecules and blockade of others, which interferes with the normal circulation of ions towards one or more electrodes, thereby accumulating inside the channel ions that are not allowed to pass through the semi-permeable membrane, but not accumulating those which are attracted by the respective counterpart electrode, and by this means generating at least two zones with different ionic strength, conductivity and local electric field strength; whereby the zone having a lower electric field strength is situated upstream from the one having a higher electric field strength;

applying a hydrodynamic force to the channel, said hydrodynamic force being greater than and opposed to the electrical force generated on the charged molecules of interest situated at the zone with lower local electric field strength; therefore pushing the charged molecules of interest downstream towards the zone with higher electric field strength, and lower than and in opposition to the electrical force generated in the zone with higher electric field strength, resulting in that the charged molecules of interest are pushed back up-stream towards the zone with lower electric field strength; where the process is repeated, thereby stacking the ions between the zones with different electric field strengths;

the zone with higher electric field strength is situated upstream from the one with lower electric field strength; wherein charged molecules, attracted by the upstream electrode, are pulled with an electrical force greater than the hydrodynamic force of the flow stream, and not allowed to pass through the ion selective membrane, are retained on the surface of the membrane.

2. The method of claim 1, wherein the electrically non-conductive channel contains a zone where the velocity of the flow stream is lower than in the rest of said channel; wherein said zone is situated downstream from the zone with lower electric field strength; and the zone with higher electric field strength is situated in the region where the velocity of the flow stream is lower; thereby capturing the molecules of interest, at the boundary of the zones with lower and higher velocity of the flow stream, that can move upstream if they are situated in the area with lower velocity of the flow stream (and higher electric field), but cannot enter the area with higher velocity of the flow stream (and lower electric field).

3. The method of claim 2, wherein the charged molecules of interest are released by modifying the applied flow rate and/or electrical field and/or by changing the electrolytic medium to a medium with a different ionic strength, pH or conductivity.

4. The method of claim 3, wherein several electrodes and corresponding ion selective membranes are present in the channel, and that different electric fields are applied between the electrodes; creating several zones with different local electric field strengths, so that different charged molecules of interest with different electric mobilities are captured at different zones along the fluidic channel, whereafter;

said electric fields differences are removed between; one pair of electrodes after the other, or all at the same time, thereby; releasing said molecules, captured at different zones along the fluidic channel, sequentially or all at the same time, respectively.

5. The method according to claim 4, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

6. The method according to claim 3, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

7. The method of claim 2, wherein molecules with different mobility are separated by modifying the applied flow rate and/or electrical field and/or by changing the electrolytic medium to a medium with a different ionic strength, pH or conductivity.

8. The method of claim 7, wherein several electrodes and corresponding ion selective membranes are present in the channel, and that different electric fields are applied between the electrodes; creating several zones with different local electric field strengths, so that different charged molecules of interest with different electric mobilities are captured at different zones along the fluidic channel, whereafter;

said electric fields differences are removed between; one pair of electrodes after the other, or all at the same time, thereby;

releasing said molecules, captured at different zones along the fluidic channel, sequentially or all at the same time, respectively.

9. The method according to claim 8, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

10. The method according to claim 7, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

11. The method according to claim 2, wherein several electrodes and corresponding ion selective membranes are present in the channel, and that different electric fields are applied between the electrodes; creating several zones with different local electric field strengths, so that different charged molecules of interest with different electric mobilities are captured at different zones along the fluidic channel, whereafter;
- said electric fields differences are removed between; one pair of electrodes after the other, or all at the same time, thereby;
- releasing said molecules, captured at different zones along the fluidic channel, sequentially or all at the same time, respectively.

12. The method of claim 11, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

13. The method of claim 2, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

14. The method of claim 1, further comprising the step of releasing the charged molecules of interest by at least one of modifying the applied flow rate, modifying the electrical field and changing the electrolytic medium to a medium with a different ionic strength, pH or conductivity.

15. The method according to claim 14, wherein several electrodes and corresponding ion selective membranes are present in the channel, and that different electric fields are applied between the electrodes; creating several zones with different local electric field strengths, so that different charged molecules of interest with different electric mobilities are captured at different zones along the fluidic channel, whereafter;
- said electric fields differences are removed between; one pair of electrodes after the other, or all at the same time, thereby;
- releasing said molecules, captured at different zones along the fluidic channel, sequentially or all at the same time, respectively.

16. The method of claim 15, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

17. The method of claim 14, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

18. The method of claim 1 further comprising the step of separating molecules with different mobility by at least one of modifying the applied flow rate, modifying the electrical field and changing the electrolytic medium to a medium with a different ionic strength, pH or conductivity.

19. The method according to claim 18, wherein in that several electrodes and corresponding ion selective membranes are present in the channel, and that different electric fields are applied between the electrodes; creating several zones with different local electric field strengths, so that different charged molecules of interest with different electric mobilities are captured at different zones along the fluidic channel, whereafter;
- said electric fields differences are removed between; one pair of electrodes after the other, or all at the same time, thereby;
- releasing said molecules, captured at different zones along the fluidic channel, sequentially or all at the same time, respectively.

20. The method of claim 19, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

21. The method of claim 18, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

22. The method of claim 1, wherein several electrodes and corresponding ion selective membranes are present in the channel, and that different electric fields are applied between the electrodes; creating several zones with different local electric field strengths, so that different charged molecules of interest with different electric mobilities are captured at different zones along the fluidic channel, whereafter;
- said electric fields differences are removed between; one pair of electrodes after the other, or all at the same time, thereby; releasing said molecules, captured at different zones along the fluidic channel, sequentially or all at the same time, respectively.

23. The method of claim 22, wherein the channel is divided into one or more sub-channels, each comprising one or more electrodes and the corresponding ion selective membranes, and that molecules are stacked and released in the channels and guided along one or more sub-channels by modifying the electric field between the ion selective membranes.

24. The method of claim 1, whereby the channel is divided into one or more sub-channels, each comprising one or more electrodes and the corresponding ion selective membranes, and that molecules are stacked and released in the channels and guided along one or more sub-channels by modifying the electric field between the ion selective membranes.

25. The method of claim 24 whereby the sub-channels further comprise one or more inlet and outlet and that molecules are stacked and released in the channels and guided along one or more sub-channels by modifying the applied flow rate and/or electrical field and/or by changing the electrolytic medium to a medium with a different ionic strength or conductivity.

26. The method of claim 1 further comprising the step of replacing an electrolyte medium for a second medium by means of injecting another fluid media into the fluidic channel while the charged molecules of interest are captured.

27. The method of claim 26, wherein different media are injected sequentially into the fluidic channel in order to perform several and/or multistep-based: interactions and/or reactions and/or medium replacement.

28. The method of claim 27, whereby sample cleanup, reduction, alkylation and proteolytic digestion is performed on-line.

29. The method of claim 26, whereby the second medium contains less salt, allowing desalting of the charged molecules of interest.

30. The method of claim 26, whereby the second medium contains molecules that are brought into contact with charged molecules of interest and interact and/or react.

31. The method of claim 26, whereby other molecules of interest are captured and brought into contact with the primary captured charged molecules of interest.

32. The method of claims 30 or 31, whereby the molecules brought into contact are the following pairs of molecules: antigen (antibody), antibody (antigen), hormone (hormone receptor), hormone receptor (hormone), polynucleotide (complementary polynucleotide), avidin/streptavidin (biotin), biotin (avidin/streptavidin), enzyme (enzyme substrate), enzyme substrate (enzyme), enzyme (enzyme inhibitor), enzyme inhibitor (enzyme), lectins (carbohydrate), carbohydrate (lectins), lipid (lipid binding protein), lipid binding protein (lipid), lipid (membrane-associated protein), membrane-associated protein (lipid), polynucleotide (polynucleotide binding protein), polynucleotide binding protein (polynucleotide), receptor (neurotransmitter), neurotransmitter (receptor), drug (target), target (drug), protein (protein), protein (polynucleotide), polynucleotide (protein), DNA (DNA), DNA (RNA), RNA (DNA), DNA (protein), protein (DNA), RNA (protein) and protein (DNA).

33. The method of claims 30 or 31, whereby the molecules react in a synthesis, or degradation.

34. The method of claims 30 or 31, whereby the reaction is proteolytic digestion of a protein.

35. The method of claims 30 or 31, whereby the reaction is any structural modification of a protein or a peptide.

36. The method of claims 30 or 31, whereby the reaction is any structural modification of DNA or RNA.

37. The method of claim 30 or 31, whereby the reaction is DNA, RNA, protein or peptide synthesis.

38. The method of claim 30 or 31, whereby the reaction is DNA, RNA, protein or peptide sequencing.

* * * * *

UNITED STATES PATENT AND TRADEMARK OFFICE
CERTIFICATE OF CORRECTION

PATENT NO. : 7,731,827 B2  Page 1 of 1
APPLICATION NO. : 11/155150
DATED : June 8, 2010
INVENTOR(S) : Juan Astogra-Wells et al.

It is certified that error appears in the above-identified patent and that said Letters Patent is hereby corrected as shown below:

On the Title Page, column 1, below "US 2005/0284762 Al Dec. 29, 2005",

Insert Item --(30) Foreign Application Priority Data

SWEDEN PCT/SE03/02027 12/19/2003

SWEDEN SE 0203773-7 12/19/2002--.

On the Title Page, column 2 (Abstract), line 11, delete "it", insert --It--.

Signed and Sealed this

Fourteenth Day of September, 2010

David J. Kappos
*Director of the United States Patent and Trademark Office*